US008026348B2

(12) United States Patent
Lesnikowski et al.

(10) Patent No.: US 8,026,348 B2
(45) Date of Patent: Sep. 27, 2011

(54) NUCLEOSIDE DERIVATIVE, MODIFIED OLIGONUCLEOTIDE, METHOD FOR THEIR SYNTHESIS AND APPLICATIONS THEREOF

(76) Inventors: Zbigniew J. Lesnikowski, Lodz (PL); Agnieszka Olejniczak, Lodz (PL)

( * ) Notice: Subject to any disclaimer, the term of this patent is extended or adjusted under 35 U.S.C. 154(b) by 804 days.

(21) Appl. No.: 10/555,351

(22) PCT Filed: Apr. 30, 2004

(86) PCT No.: PCT/PL2004/000030
§ 371 (c)(1),
(2), (4) Date: Aug. 8, 2006

(87) PCT Pub. No.: WO2004/096824
PCT Pub. Date: Nov. 11, 2004

(65) Prior Publication Data
US 2007/0009889 A1    Jan. 11, 2007

(30) Foreign Application Priority Data

May 2, 2003 (PL) .......................... 359949
May 20, 2003 (PL) .......................... 360228

(51) Int. Cl.
*C07H 19/073* (2006.01)
*C07H 19/173* (2006.01)
*C07H 21/04* (2006.01)

(52) U.S. Cl. ..................... 536/23.1; 536/24.3; 536/25.3; 536/25.31; 536/25.34; 536/26.6; 536/26.7; 536/26.8; 536/27.6; 536/27.81; 536/28.5; 536/28.53; 536/28.54

(58) Field of Classification Search .................. None
See application file for complete search history.

(56) References Cited

U.S. PATENT DOCUMENTS

| | | | |
|---|---|---|---|
| 5,171,849 A | 12/1992 | Soloway et al. | |
| 5,405,598 A | 4/1995 | Schinazi et al. | |
| 5,466,679 A | 11/1995 | Soloway et al. | |
| 5,599,796 A * | 2/1997 | Schinazi et al. | 514/44 A |
| 6,180,346 B1 | 1/2001 | Thorp | |
| 6,180,766 B1 * | 1/2001 | Schinazi et al. | 536/22.1 |
| 6,361,951 B1 | 3/2002 | Thorp et al. | |
| 6,391,558 B1 | 5/2002 | Henkens et al. | |
| 6,583,122 B2 * | 6/2003 | Schinazi et al. | 514/44 A |
| 6,806,363 B1 * | 10/2004 | Collins et al. | 536/26.4 |
| 7,468,432 B2 * | 12/2008 | Collins et al. | 536/26.4 |

FOREIGN PATENT DOCUMENTS

| | | |
|---|---|---|
| JP | 2000125865 | 5/2000 |
| JP | 2001013103 | 1/2001 |
| JP | 2001064298 | 3/2001 |
| JP | 2002000299 | 1/2002 |
| JP | 2002080491 | 3/2002 |
| WO | WO-0031101 | 6/2000 |
| WO | WO-0107665 | 2/2001 |
| WO | WO-02053571 | 7/2002 |
| WO | WO-02057488 | 7/2002 |

OTHER PUBLICATIONS

Agrawal, S., ed., "Antisense Therapeutics" (1996), *Humana Press*, Totowa, N.J., Tbl./Cnt only.
Agrawal, S., ed., Protocols for Oligonucleotides and Analogs Synthesis and Properties (1993), *Humana Press Inc* ., Totowa, N.J., Table of Contents only.
Anthony, R.M., Brown, T.J., French, G.L., "DNA Arrary Technology and Diagnostic Microbiology" (2001), *Expert. Rev. Mol. Diagn..*, 1,30-38.
Bigey P., Holst Sonnichsen, S., Meunier, B., Nielsen, "P.E. DNA Binding and Cleavage by a Cationic Manganese Porphirin-Peptide Nucleic Acid Conjugate" (1997), *Bioconjugate Chem.*, 8, 267-270.
Cotter, F.E., ed., "Molecular Diagnosis of Cancer" (1996), *Human Press*, Totowa, N.J., T/C only.
Crooke, S.T., "Therapeutic Applications of Oligonucleotides" (1995), *Springer-Verlag*, New York, Table of Contents only.
Denhardt, D.T., "A Membrane Filter Technique for the Detection of Complementary DNA" (1966), *Biochem. Biophys. Res. Commun.*, 23, 641-646.
Dougan, H., Hobbs, J.B., Weitz, J.I., Lyster, D.M., "Synthesis and Radioiodination of Stannyl Oligodeoxyribonucleotide" (1997), *Nucl. Acids. Res.*, 25, 2897-2901.
Dubey, I., Pratviel, G., Meunier, B., "Synthesis and DNA Cleavage of 2'-O-amino-linked metalloporphirin-oligonucleotide conjugates" (2000), *J. Chem. Soc. Perkin Transactions*, Iss 18, 3088-3095.
Ehrlich, G.D., Greenberge, S.J., "PCR-Based Diagnostics in Infections Disease" (1994), *Blackwell Scientific Publications*, Oxford, UK, Table of Contents only.
Elles, R., ed., "Molecular Diagnosis of Genetic Diseases" (1996), *Huumana Press* , Totowa, N.J., Table of Contents only.
Fulcrand-El Kattan, G., Lesnikowski, Z.J., Yao, S., Tanious, F., Wilson, W.D., Shinazi, R.F., "Carboranyl Oligonucleotides 2. Synthesis and Physicochemical Properties of Dodecathymidylate Containing 5-(o-Carboranyl-1-yl)-2'-O-Deoxyuridine" (1994), *Am. Chem. Soc.*, 116, 7494-7501.
Grimes, R.N., "Transition Metal Metallacarboranes" in,, Coomprehensive organometallic Chemistry II (1995), vol. 1, *Housecroft, C.E., Ed. Pergamon*, pp. 373-430.
Hall, I.H., Tolmie C.E., Barnes B.J., Curtis M.A., Russell J.M., Finn M.G., Grimes R.N., "Cytotoxicity of tantalum (V) and niobium (V) small carborane complexes and mode of action in P388 lyphocytic leukemia cells" (2000), *Applied Organometallic Chem.*, 14, 108-118.
Hall, B.D., Spiegelman, S., "Sequence Complementarity of T2-DNA and T2-specific RNA" (1961), *Proc. Natl. Acad. Sci. USA*, 47, 137-146.
Hoheisel, J.D., "Oligomer-Chip Technology" (1997), *Tiibtech*, 15-465-469.

(Continued)

*Primary Examiner* — Lawrence E Crane
(74) *Attorney, Agent, or Firm* — Nutter McClennen & Fish LLP; William C. Geary, III

(57) ABSTRACT

Compositions and methods of preparing carboranes and metallacarboranes, which can be used as a new type of electrochemically active label for biological compounds, are disclosed. Nucleic acid derivatives labelled with carborane or metallacarborane can be detected by electrochemical methods and can find several practical applications, such as materials for nanoconstruction, in DNA array technology or for the construction of biosensors, especially electrochemical biosensors. Other applications can include use as modified primers in amplification of RNA and DNA, antisense drugs, boron carriers for BNCT, radiopharmaceuticals bearing a range of isotopes useful in different types of radiotherapy, molecular probes, elements of biosensors, materials for nanotechnology and others.

33 Claims, 13 Drawing Sheets

OTHER PUBLICATIONS

Hosman, N.S., Maguire, J.A., "Recent Advances in the Chemistry of Main Group Heterocarboaranes" in ,, Advances in Boron and the Boranes (1987), *Liebman, J.F., Greenberg, A., Williams, R.E., ed. VCH.*, str. 297-329.

Housecroft, C.E., "Boranes and Metalloboranes—Structure, bonding and reactivity" (1990), *John Wiley and Sons*, New York, N.Y., Table of Contents only.

Hurley, D.J., Tor, Y., "Metal-containing Oligonucleotides: Sold-Phase Synthesis and Luminescence properties" (1998), *J. Am. Chem. Soc.*, 120-2194-2195.

Ihara, T., Maruo, Y., Takenaka, S., Takagi, M. (1996), "Ferocene-oligonucleotide conjugates for electrochemical probing of DNA", *Nuc. Acids Res.*, 24, 4273-4280.

Ihara, T., Nakayama, M., Murata, M., Maeda, M. "Gene Sensor Using Ferrocenyl Oligonucleotide" (1997), *Chem. Commun.*, 1609-1610.

Jefferies D.J., De Clerq, E., ed., "Antiviral Chemotherapy" (1995), *John Wiley and Sons*, Chichester UK., Table of Contents only.

Keller, G.H., Manak, M.M., "DNA Probes. Background, Applications and Procedures" (1993), *M Stockton Press*, New York, N.Y., Table of Contents only.

Lesnikowski, Z.J. and Schinazi, R.F., "Boron Neutron Capture Therapy of Cancers: Necleic Bases, Nucleosides, and Oligonucleotides as Potential Boron Carriers" (1995), *Polish J. Chem*, 69, 827-840.

Lesnikowski, Z.J., Fulcrand-El Kattan, G., Lloyd, R.M. Jr., Juodawlkis A., Schinazi R.F., "Carboranyl Oligonucleotides. 3. Biochemical Properties of Oligonucleotides Containing 5-(o-carbaoranyl-l-yl)-2'-deoxyuridine" (1996b), *Biochemistry*, 35, 5741-5746.

Lesnikowski, Z.J., Fulcrand-El Kattan, G., Lloyd, R.M. Jr., Schinazi, R.F., "Biological Properties of Dodeca(thymidine Phosphates) Containing 5-(o-Carboaran-1-yl)-2'-deoxyuridine" (1996), *Phosphorus, Sulfur, and Silicon*, 109-110, 385-388.

Lesnikowski, Z.J., Lloyd, R.M. Jr., Schinazi, R.F., "Comparison of Physiocochemical Properities of (o-Carboran-1-yl)methylophosphonate and Methylphosphonate Oligo-nucleotides" (1997), *Nucleosdies and Nucleotides*, 16, 1503-1505.

Lesnikowski, Z.J., Schinazi, R.F., "Carboranyl Oligonucleotides. 1. Synthesis of Thymidine (o-carboranyl-l-yl)methylphosphonate" (1993), *J. Org. Chem.*, 58: 6531-6534.

Lesnikowski, Z.J., Shi J. Schinazi R.F., "Nucleic Acids and Nucleosides Containing Carboranes" (1999), *J. Organomet. Chem.*, 581, 156-169.

Lipschutz, R.J., Morris, D., Chee, M., Hubbell, E., Kozal, M.J.>, Shah, N., Shen, N., Yang, R., Fodor, S.P.A., "Using Oligonucleotide Probe Arrays to Access Genetic Diversity" (1995), *BioTechniques*, 19, 442-447.

Mack, D.P., Iverson, B.L., "Dervan, P.B. Design and Chemical Synthesis of a Sequence-Specific DNA-Cleaving Proten" (1988), J. Am. Chem. Soc., 110, 7572-7474.

Micklefield, J., "Backbone Modification of Nucleic Acids: Synthesis, Structure and Therapeutic Applications" (2001), *Current Med. Chem.*, 8, 1157-1179.

Niemeyer, C.M., "DNA as a Material for Nanotechnology" (1997), *Angew. Chem. Int. Ed. Engl.*, 36, 585-587.

Olejniczack A.B., Koziolkiewicz M. Lesnikowski Z.J., "Carboranyl Oligonucleotides. 4. Synthesis, and Physiochemical Studies of Oligonucleotides containing 2' -0(o-carboran-1-yl)methyl group ", *Antisense Nucl. Acid Drug Develop.*, 2002, 12, 79-94.

Ossipov, D., Pradeepkumar, P.I., Holmer, M., Chattopadhyaya, J., "Synthesis of [Ru(phen)2dppz]2+ tethered oligo-DNA and studies on the metallointercalation mode into the DNA duplex" (2001), *J. Am. Chem. Soc.*, 123, 3551-3562.

Sanghvi Y.S., Cook, P.D., ed., "Carbohydrate Modifications in Antisense Research" (1994), *American Chemical Society*, Washington, D.C., Table of Contents only.

Saxena A.K., Hosmane N.S., "Recent Advances in the Chemistry of Carborane Metal Complexes Incorporating d- and f-Block Elements" (1993), *Chem. Rev.*, 93, 1081-1124.

Schinazi, R.F., Lesnikowski, Z.J., Boron Containing Oligonucleotides (1998), Nucleosides & Nucleotides, 17(1-3), 635-647.

Seeman, N., Wang Hui, et al., "New Motifs in DNA Nanotechnology" (1998), *Nantechnology* 9, 257-273.

Shabarova, Z., and Bogdanov, A.,"Advanced Organic Chemistry of Nucleic Acids" (1994), *VCH*, Weinheim., Table of Contents only.

Singhal, P., Kuhr, W.G., "Ultrasensitive Voltametric Detection of Underivatized Oligonucleotides and DNA" (1997), *Ana. Chem.*, 69, 4828-4832.

Steel, A.B., Herne, M.T., Tarlov, M.J., "Electrochemical Quantitation of DNA Immobilized on Gold" (1998), *Anal. Chem.*, 70, 4670-4677.

Strobel, S.A., Heinz, E.M., Dervan, P.B., "Double-Strabd Cleavage of Genomic DNA at a Single Site by Triple-Helix Formation" (1988), *Am. Chem. Soc.*, 110, 7927-7929.

Takenaka, S., Uto, Y., Kondo, H., Ihara, T., Takagi, M., "Electrochemically Active DNA Probes: Detection of Target DNA Sequences at Femtomole Level by High-Performance Liquid Chromatography with Electrochemical Detection" (1994), *Anal. Biochem.*, 218, 436-443.

Tjarks, W., "The Use of Boron Clusters in the Rational Design of Boronated Nucleosides for Neutron Capture Therapy of Cancer"(2000), *J.Organomet. Chem.*, 614-615, 37-47.

Uhlmann, E., Peymann, A.. Antisense Oligonucleotides—A New Therapeutic Principle (1990), *Chem. Rev.*, 90, 543-584.

Wang, J., Cai, X., Fernandez, J.R., Grant, D.H., Ozsoz, M., "Electrochemical Measurements of Oligonucleotides in the Presence of Chromosomal DNA Using Membrane-Covered Carbon Electrode"(1997), 69 4056-4059.

Wiedbrauuk, D.L., Farkas, D.H., ed., "Molecular Methods for Virus Detection" (1995), *Academic Press, Inc.*, San Diego, C.A., Table of Contents only.

Yu, C.J., Yowanto, H., Wan, Y., Meade, T.J., Chong, Y., Strong, M., Donilon, L.H., Kayyem, J.F., Gozin, M., Blackburn, G.F., "Uridine-Conjugated Ferrocene DNA Oligonucleotides: Unexpected Cyclization Reaction of the Uridine Base" (2000), *J. Am. Chem. Soc.*, 122. 6767-6768.

Grimes, R., "Metallacarboranes in the New Millennium", Coordination Chemistry Reviews, 200-202, pp. 773-811, (2000).

Grimes, R., "Transition Metal Metallacarbaborones", Comprehensive Organometallic Chemistry II, vol. 1, pp. 373-427, (1982-1994).

Olejniczak, A. B., et al., "Carboranyl Oligonucleotides: 4. Synthesis and Physicochermical Studies of Oligonucleotides Containing 2'-O-(o-Carboran-l-yl)Methyl Group", Antisense & Nucleic Acid Drug Development, vol. 12, pp. 79-94 (2002).

Saxena, A. et al., "Recent Advances in the Chemistry of Heterocarborane Complexes Incorporating s- and p-Block Elements", Chem. Rev., vol. 97, pp. 2421-2461 (1997).

Schinazi, R. et al., "Carboranyl Oligonucleotides for Antisense Technology and Boron Neutron Capture Therapy of Cancers", American Chemical Society Symposium Series, vol. 580, Carbohydrate Modifications in Antisense Research, Sanghvi Y S, Cook PD, Eds., Chapter 11, pp. 169-182 (1994).

Sneath et al., Inorganic Chemistry, vol. 12, No. 1, pp. 44-48, 1973.

Green, Polymer Letters, vol. 2, pp. 109-113, 1964.

\* cited by examiner

SEQUENCE LISTING

```
<160> NUMBER OF SEQ ID NOS: 4

<210> SEQ ID NO 1
<211> LENGTH: 14
<212> TYPE: DNA
<213> ORGANISM: Artificial sequence
<220> FEATURE:
<223> OTHER INFORMATION: Synthetic construct
<220> FEATURE:
<221> NAME/KEY: modified_base
<222> LOCATION: (1)..(1)
<223> OTHER INFORMATION: n = t modified by BCCo
      {diethyleneoxy-8{[(1,2-dikarba-closo-undekaborane)-3,3'-cobalt-
      (1',2'-dikarba-closo-undekaborane)ate]}
<220> FEATURE:
<221> NAME/KEY: misc_feature
<222> LOCATION: (1)..(1)
<223> OTHER INFORMATION: n is a, c, g, or t

<400> SEQUENCE: 1
ngctggtttg gctg                                                    14

<210> SEQ ID NO 2
<211> LENGTH: 14
```

```
<212> TYPE: DNA
<213> ORGANISM: Artificial sequence
<220> FEATURE:
<223> OTHER INFORMATION: Synthetic construct
<220> FEATURE:
<221> NAME/KEY: modified_base
<222> LOCATION: (1)..(1)
<223> OTHER INFORMATION: n = t modified by BEC
      4-o-(diethyleneoxy-8-COSAN)
<220> FEATURE:
<221> NAME/KEY: misc_feature
<222> LOCATION: (1)..(1)
<223> OTHER INFORMATION: n is a, c, g, or t

<400> SEQUENCE: 2
ngctggtttg gctg                                                       14

<210> SEQ ID NO 3
<211> LENGTH: 14
<212> TYPE: DNA
<213> ORGANISM: Artificial sequence
<220> FEATURE:
<223> OTHER INFORMATION: Synthetic construct

<400> SEQUENCE: 3
cgctggtttg gctg                                                       14

<210> SEQ ID NO 4
<211> LENGTH: 14
<212> TYPE: DNA
<213> ORGANISM: Artificial sequence
<220> FEATURE:
<223> OTHER INFORMATION: Synthetic construct
<220> FEATURE:
<221> NAME/KEY: modified_base
<222> LOCATION: (13)..(13)
<223> OTHER INFORMATION: n = u modified by 2'-CBM
      2'-nido-(o-carboran-1-yl)methyl
<220> FEATURE:
<221> NAME/KEY: misc_feature
<222> LOCATION: (13)..(13)
<223> OTHER INFORMATION: n is a, c, g, or t

<400> SEQUENCE: 4
cgctggtttg gcng                                                       14
```

NUCLEOSIDE DERIVATIVE, MODIFIED OLIGONUCLEOTIDE, METHOD FOR THEIR SYNTHESIS AND APPLICATIONS THEREOF

CROSS REFERENCES TO RELATED APPLICATIONS

This application claims benefit of priority to PCT International Application No. PCT/PL04/00030, filed on Apr. 30, 2004, entitled "Nucleoside derivative, modified oligonucleotide, method of their synthesis and applications thereof" and Polish Patent Application No: P359949, filed on May 2, 2003 and Polish Patent Application No: P360228 filed on May 20, 2003, the contents of which are hereby incorporated by reference in their entirety.

FIELD OF THE INVENTION

This invention is in the area of synthetic organic chemistry, and in particular conjugates of nucleosides and oligonucleotides with boron clusters containing metals and other elements and theirs isotopes, their molecular structure and method of preparation and use.

The invention also concerns the application of carboranes and metallacarboranes as a new type of electrochemically active label for biological compounds. The derivatives labelled with a carborane or metallacarborane can be detected by electrochemical methods and may find several other practical applications, specifically as materials for nanoconstruction, in DNA array technology or for the construction of biosensors, especially electrochemical biosensors.

BACKGROUND OF THE INVENTION

Nucleosides and nucleotides, components of nucleic acids, and oligonucleotides (short stretches of nucleic acids) find broad application among others, in biology, medicine and nanotechnology (Agrawal, 1996; Cotter, 1996; Crooke, 1995; Ells, 1996; Jefferies and De ClercQ, 1995; Keller and Manak, 1993; Niemeyer, 1997; Seeman et al, 1998; Wiedbrauk and Farkas, 1995).

Due to the different requirements dependent upon specific applications of oligonucleotides and their components, natural nucleosides, nucleotides and oligonucleotides are modified in order to obtain molecules with designed and needed properties. Essentially all parts of the nucleoside, nucleotide and oligonucleotide can be modified, namely the sugar residue, nucleic base and phosphate group (Agrawal, 1993; Micklefield, 2001; Shabarova and Bogdanov, 1994; Sanghvi and Cook, 1994; Uhlmann, E., Peyman, A., 1990).

One of the modifications is based on the use of boron clusters such as carboranes, as the modifying entity. The carborane group can be attached to the nucleoside unit directly or through a linker. Most nucleosides modified with a carborane group belong to a pyrimidine nucleoside family. (Lesnikowski i Schinazi, 1995; Tjarks, W., 2000).

Three types of carboranyl group ($-C_2B_{10}H_{12}$) containing DNA-oligonucleotides have been described so far: 1) (o-carboran-1-yl)methylphosphonate-oligonucleotides (CBMP-oligonucleotides), consisting of a carborane cage within an internucleotide linkage (Lesnikowski and Schinazi, 1993; Lesnikowski et al, 1997; Lesnikowski, 2003), 2) 5-(o-carboran-1-yl)-2'-deoxyuridine-oligonucleotides (CDU-oligonucleotides) containing a carborane cage attached to a nucleobase (Fulcrand-El Kattan et al, 1994; Lesnikowski et al, 1996; Lesnikowski, 2003), and 3) 2'-O-(o-carboran-1-yl) methyl-oligonucleotides (2'-CBM-oligonucleotides) with a carborane cage linked to a sugar residue at 2' position (Olejniczak et al, 2002; Olejniczak and Lesnikowski, 2002; Lesnikowski, 2003). Other types of modified nucleosides, nucleotides and oligonucleotides are derivatives of these compounds consisting of metal complexes (Bigey et al., 1997; Dervan et al., 1988; Dougan et al., 1997; Dubey et al., 2000; Hurley and Tor, 1998; Ossipov et al, 2001; Strobel et al, 1988; Yu et al, 2000). Nucleoside conjugates containing metal complexes with ligands other than a carborane cage or nucleosides containing a carborane cage without a metal ion have been described. For example, U.S. Pat. No. 6,180,766 discloses nucleosides and oligonucleotides containing boron clusters. Application of these derivatives as boron carriers for BNCT of tumors, antisense biotherapeutics and molecular probes in medical diagnostics are proposed.

Application WO 2002053571 describes new derivatives of polycyclic hydrocarbons and naphthalene imides type of ferrocene and methods of their synthesis, their intercalating properties, method for their electrochemical detection and several examples of practical applications. The disclosed compounds are easy for synthesis and purification, and are efficient intercalators towards double stranded DNA and RNA. However, as an electrochemical label it binds to a nucleic acid molecule through weak intercalating interactions, substantially limiting the practical utility of the proposed compounds.

The subject of JP 2001064298 is the preparation of oligonucleotide/ferrocene conjugates and their application for electrochemical detection of DNA. Disclosed is a method for synthesis of conductively or electrochemically active oligonucleotides. Oligonucleotides are transformed into an organic solvent soluble form via ion pair formation with suitable lipids and are treated with a type of ferrocene monocarboxylic acid N-hydroxy succinimide ester compound. Though, in the invention described above, the method for the synthesis of oligonucleotide conjugates containing a metal ion is limited to the incorporation into the oligonucleotide molecule iron only.

In the U.S. Pat. No. 5,599,796 the method and compounds for treating urogenital tumors, and particular, cancer of the prostate, bladder, and kidney with BCNT, are disclosed. Preferred boron carriers include 5-carboranyl-2'-deoxyuridine (CDU) and 5-o-carboranyl-1-(2-deoxy-2-fluoro-b-D-arabinofuranosyl)uracil (CFAU). Nucleosides and oligonucleotides bearing an —O-[(carboran-1-yl)alkyl]phosphate, S-[(carboran-1-yl)alkyl]phosphorothioate, or Se-[(carboran-1-yl)alkyl]phosphoroselenoate in place of the (carboran-1-yl) phosphonate moiety can be used.

Oligonucleotides of specific gene sequences that include one or more 3',5'-linking-(carboran-1-yl)phosphonate moieties can also be used in antisense therapy in the selective modification of gene expression. The therapy is accomplished by administering the boron-containing compound by any appropriate route, including by intravenous injection, oral delivery or by catheter or other direct means, in such a manner that the compound accumulates in the target tumor. After desired accumulation of the compound in the tumor, the site is irradiated with an effective amount of low energy neutrons.

In the application JP 2002080491 preparation of electrophilic boron-containing nucleotide analogs and their intermediates is disclosed. Described nucleotide anlogues of general structure $(HO)_2BX[P(O)(O—)O]nNu$ (1; Nu=nucleoside residue; X=$CF_2$, CH2; n=2, 3) are prepared by difluoromethylation of $HP(O)(OR1)2$ (R1=alkyl), reaction with (R2O)3B (R2=lower alkyl), deprotection, protection with 1,2-diols, coupling with nucleotides, and deprotection.

Application U.S. Pat. No. 5,130,302 is focused on boronated nucleoside, nucleotide and oligonucleotide compounds, compositions and methods for using the same. A novel class of pharmaceutically active boronated nucleosides are provided. The nucleosides are boronated at a nitrogen of the purine or pyrimidine ring or analogues thereof. Also provided are phosphate esters of these nucleosides and oligomers thereof. Methods of making and use of the boronated nucleosides are also disclosed. Both of the above applications provide method for the synthesis of some boron containing nucleoside derivatives, but does not allow incorporation of more than one boron atom per modification and does not permit incorporation into a modified molecule other than boron metals.

U.S. Pat. No. 5,466,679 discloses carboranyl uridines and their use in BNCT. The invention relates to novel boron-containing nucleosides and amino acids which can utilize the enzymatic systems in tumor cells for incorporating such boron-containing structures into nucleic acids and proteins. Subsequent use of boron neutron capture therapy provides a method for treatment of tumor cells. The subject of U.S. Pat. No. 5,171,849 is 2' and 3' carboranyl uridines and their diethyl ether adducts. Disclosed is also a process for preparing carboranyl uridine nucleoside compounds and their diethyl ether adducts which exhibit a tenfold increase in boron content over prior art boron containing nucleoside compounds. Said carboranyl uridine nucleoside compounds exhibit enhanced lipophilicity and hydrophilic properties adequate to enable solvation in aqueous media for subsequent incorporation of said compounds in methods for boron neutron capture therapy in mammalian tumor cells. In the U.S. Pat. No. 5,405,598 new sensitizing agents for use in boron neutron capture therapy are proposed. In spite that the compound proposed in the last three applications contain tenfold more boron atoms than described earlier derivatives consisting boric acid residue, the compounds still contain twofold less than proposed in the present invention. It should be also pointed out that any of the methods proposed so far do not allow incorporation into designed biomolecule such as nucleoside, nucleic acid or other broad spectrum of different metal ions.

Nucleic acid hybridization technology essentially began with the work of Hall and Spiegelman (Hall and Spiegelman, 1961). Originally, the probe and target were hybridized in a solution and the hybrids were isolated by equilibrium-density gradient centrifugation. This procedure was slow, labor-intensive and inaccurate. Substantial progress has been achieved due to the development of the first solid phase hybridization method (Denhardt, 1966). Extensive studies during next 20 years yielded new, automated techniques for hybridization technology. The advancement was possible mainly due to improved attachment methods of DNA/RNA or DNA-oligonucleotide probes to solid support and better methods of their labeling and detection (Keller and Manak, 1993). The most frequently used labels were radioactive isotopes such as $^{32}P$, $^{3}H$, $^{14}C$ and $^{35}S$, fluorescent compounds and dyes absorbing visible light, and the most often used test format was the ELISA type immunoenzymatic assay. Comparison of selected methods are shown in Table 1.

TABLE 1

Comparison of sensitivity of selected methods used for DNA detection.

| Enzyme | Label | Method of detection | Sensitivity |
|---|---|---|---|
| Alkaline phosphate | 4-nitrophenyl | Colorimetric | 5 fmol |
| Alkaline phosphate | NBT/BCIP | Colorimetric | 0.5 fmol |
| Horse-radish peroxidase | o-Phenylenediamine | Colorimetric | 0.1 fmol |
| Horse-radish peroxidase | Luminol | Colorimetric | 1.0 fmol |
| Horse-radish peroxidase | ENH/LUM | Chemiluminescence | 0.05 fmol |
| — | $^{32}P$ | Scintillation | 0.05 fmol |
| — | Fluoroscein | Fluorimetry | 500 fmol |
| — | Texas red | Fluorimetry | 100 fmol |
| — | Rodamine | Fluorimetry | 100 fmol |
| — | Isoluminol | Chemiluminescence | 100 fmol |
| — | metal ions | Voltammetry | 1 fmol[b] |

[a]Urdea M S., Warner B D., Running J A., Stempien M., Clyne J., Horn T., Nucl. Acids Res., 16, 4937 (1988);
[b]Ihara T., Maruo Y., Takenaka S., Takagi M., Nucl. Acids Res., 24, 4273 (1996).

At the present stage of development of labeling and detection of oligonucleotide probes, and application of such nucleic acids hybridization technology in research and medical diagnostics, plays an important role in DNA chip technology and its application in genomics (Hoheisel, 1997; Anthony et al., 2001; Lipshutz et al., 1995).

Labelling of DNA-oligonucleotide probes with electrochemical labels and their application in electrochemical detection of nucleic acids was developed only recently. Earlier attempts at electrochemical detection of nucleic acids were based on detection of natural, unlabeled nucleic acid molecules (Wang et al., 1997; Steel et al., 1998; Singhal and Kuhr, 1997). Electrochemical detection of natural nucleic acids is however nonspecific and characterized by high background. Because chemical similarities and similar nucleoside composition of oligonucleotide probes with different base sequences, selective detection of these probes without labelling is very difficult or impossible. In addition, detection of unlabeled oligonucleotide probes is hindered by the electrochemical activity of water. The ferrocene is one of a very few electrochemical labels proposed for labelling of oligonucleotide probes (Ihara et al., 1996; Ihara et al., 1997). In this case however, the label is limited to iron and its redox characteristics.

Electrochemical detection of nucleic acids is disclosed in U.S. Pat. No. 6,391,558 B1 patent dated May 21, 2002. An electrochemical detection system which specifically detects selected nucleic acid segments is described. The system utilizes biological probes such as nucleic acid or peptide nucleic acid probes which are complementary and specifically hybridize with selected nucleic acid segments in order to generate a measurable current when an amperometric potential is applied. The electrochemical signal can be quantified. In the above invention electrochemical detection of only unlabeled nucleic acids using only an amperometric method is proposed.

Nucleic acid detection methods and apparatus, and vessels for detecting nucleic acid are the subject of US 20020064795 A1 patent application dated May 30, 2002. A nucleic acid detection application is disclosed that includes a nucleic acid immobilized electrode constituted by immobilizing a nucleic acid probe to a conductor, a plurality of vessels for bringing the nucleic acid probe into contact with a subject substance, a counter electrode disposed on a bottom surface or a inside surface of the vessel, and an electric circuit for applying a voltage between the nucleic acid immobilized electrode and the counter electrode. A nucleic acid is detected by inserting the nucleic acid immobilized electrode into each vessel containing the subject substance, and using the counter electrode disposed on the bottom surface or inside surface of the vessel to electrically control the reaction.

Quantitative detection of nucleic acids by differential hybridization using electrochemical labelling of samples is described in JP 2002000299 A2 application dated Feb. 8, 2002. A method for quantitative detection of nucleic acids by differential hybridization using immobilized oligonucleotide probes complementary to nucleic acid samples labelled with conductive material, is disclosed. An electric potential is applied and current is measured by differential pulse voltammograms. DNA or PNA (peptide nucleic acid) can be used as probes. Detection of ferrocene labelled oligonucleotides (20mer of adenine, A20) using thymine 20mer probe modified with mercapto hexyl group, or PNA thymine 10 mer modified with 1,2-bis(vinylsulfonyl acetamide) ethane, is described. Hybridization-based gene detection method using intercalator and electrochemical detection of immobilized probe is described in application WO2002/057488 dated Jan. 21, 2002. The gene detection method according to the above invention is characterized in that an intercalator is introduced into the double strand, and the double strand is electrochemically detected. According to the present method, a probe and a sample gene are hybridized in a uniform solution or in a solution in the vicinity of an electrode surface, an intercalator is introduced thereinto for labeling, the probe is then immobilized on the electrode, and the amount of immobilized probe and the amount of double strand are separately detected at the same time, making it possible to accurately detect the amount in which the double strand is produced per unit amount of immobilized probe. An advantage of the present method is that reactions can be conducted with higher efficiency because the hybridization and intercalation are carried out in a solution without immobilizing the probe on the electrode.

Electrochemical detection of nucleic acid hybridization is a subject of U.S. Pat. No. 6,361,951. A method of detecting a nucleic acid (e.g., DNA, RNA) that contains at least one preselected base (e.g., adenine, guanine, 6-mercaptoguanine, 8-oxo-guanine, and 8-oxo-adenine) comprises (a) reacting the nucleic acid with a transition metal complex capable of oxidizing the preselected base in an oxidation-reduction reaction; (b) detecting the oxidation-reduction reaction; and (c) determining the presence or absence of the nucleic acid from the detected oxidation-reduction reaction at the preselected base. The method may be used in a variety of applications, including DNA sequencing, diagnostic assays, and quantitative analysis.

The requirement of the presence of one or more preselected nucleic bases in the detected DNA or RNA is a significant disadvantage of the above method. If the nucleic bases are present in the probe in nature (e.g adenine, guanine) the specificity of the detection is decreased, if they are incorporated into nucleic acids artificially—the additional procedure is required, making the process of detection more complicated. The range of the redox potentials is also limited due to the preselection of nucleic bases, making detection of several probes in the same mixture impossible.

Determination of sequence variations in nucleic acids by electrochemical detection of hybrids using probes labelled with redox groups is described in application WO 2001/007665 A2. The present invention is directed to methods and compounds for the use of self-assembled monolayers to electronically detect nucleic acids, particularly alterations such as nucleotide substitutions (mismatches) and single nucleotide polymorphisms (SNPs). The method uses arrays of probes immobilized in self-assembling monolayers on an electrode surface. Probes and target sequences are labelled with redox groups and hybridization of the probe results in a change in redox potential. Preparation of chips with probes immobilized via disulfide bridges to thiolated DNA is demonstrated and the effects of variables, such as hybridization temperature, are studied. Methods of using competimers, perfectly matching probes that will replace weak or unstable hybrids, to improve the specificity of the hybridization are described.

Electrodes coated with metal complex-containing film and its use for electrochemical detection of nucleic acid bases is described in U.S. Pat. No. 6,180,346 B1. A modified electrode prepared by electropolymerizing a film on the conductive working surface, of an electrode is disclosed. The coated electrode is used for electrochemical detection of nucleic acid bases. The electrode is modified by reductive electropolymerization of a thin film of poly[Ru(vbpy)32+] or poly[Ru(vbpy) 32+/vba] (vbpy=4-vinyl-4' methyl-2,2'-bipyridine and vba=p-vinylbenzoic acid) and the electrode is used for the electrochemical detection of aq. GMP, poly[G], and surface-immobilized single-stranded DNA probes. A DNA probe is attached covalently to the carboxylate group via a carbodiimide reaction followed by amidation of an amino-linked single-stranded DNA. In the presence of these guanine containing moieties, a dramatic enhancement in the oxidative current for the Ru3+/2+ couple (present in the polymeric thin film) due to the catalytic oxidation of guanine is observed. This invention shows example some metal complexes for detection of DNA proves their practical importance.

Electrochemical detection of the hybridization process of a probe and target nucleic with the application of the catalyst of the redox reaction attached to electrode surface is described in the application WO 2001/021635 A2. In the disclosed method DNA- or PNA-oligonucleotide probe containing catalyst of the redox reaction attached to the one end is linked to the electrode surface from the opposite side. Signal is generated as a result of hybridization of the target nucleic acid to the probe and formation of the double stranded structure allowing flow of the electric current from the electrode to the catalyst on the opposite end and initiation of the redox reaction. In this format hybridization processes can be detected using voltametric, amperometric, potentiometric or conductometric methods. Electrochemical detection of the nucleic acid hybridization process with the application of the probes coupled with electrochemical label is a subject of the application WO 2000/031101 A 1. This method can be successfully adapted for the application of electrochemical labelling of a subject of the present invention.

Methods for detecting/quantitating sample nucleic acid fragment by scanning electrochemical microscopy are described in application JP 2001013103 A2 dated Jan. 19, 2001. A highly sensitive method is provided for detecting/quantitating a sample nucleic acid fragment complementary to DNA or PNA (peptide nucleic acid) fragment immobilized on the surface by scanning electrochemical microscopy using DNA or PNA analyzing element. The sample nucleic acid is contacted with the DNA or PNA analyzing element in the presence of a hybrid DNA (or PNA)-binding electrochemical active molecule (e.g, ferrocene-modified intercalate). Then, the sample nucleic acid fragment complementary to the DNA or PNA fragment immobilized on the analyzing element as well as the electrochemical active molecule are bound to the analyzing element. The complementary sample nucleic acid fragment is detected/quantitated by measuring the electric current generated in the electrochemical active molecule-binding region on the analyzing element surface upon applying an electric potential to the analyzing element surface by a scanning electrochemical microscope. This method can be successfully adapted for the application of electrochemical labelling of a subject of the present invention.

An electrochemical method for detecting DNA using DNA sensor and intercalator is described in application JP 2000125865 A2 dated May 9, 2000. The DNA sensor comprises more than two electrodes equipped with the response terminals for output. On the surface of the electrodes, DNA probes possessing the base sequences differing from each other are immobilized. On this DNA sensor, the sample DNA dissociated into single chains are bound with the probe DNA in the presence of the electrochemical activity-embedded-type intercalator, or the intercalator is bound with the DNA hybrid formed beforehand. A DNA gene is detected by measuring the current generated through the intercalator trapped into DNA hybrid. The above method is similar to several methods mentioned earlier utilizing electrochemically labeled intercalating molecule. As a label for the intercalator molecule the electrochemical labels being a subject of the present invention can be also applied. The aim of the present invention is providing new and versatile electrochemical label, a boron cluster, in the form of a metal complex, typically metallacarborane and modified nucleosides or their derivatives comprising thereof. Application of the metallacarborane group is especially desirable because it is characterized by unusually high boron contents, and it can accommodate in its structure a broad variety of other elements, specifically metals, their ions and isotopes. This increases substantially the potential of the proposed new class of molecules beyond their use as electrochemical labels and expand the range of their practical applications. The aims have been unexpectedly achieved in the present invention.

SUMMARY OF THE INVENTION

According to the invention, a nucleoside derivative is provided that contains metallacarborane complex attached to at least one of the following constituents of the nucleoside molecule: nucleic base, sugar residue, or analogue of sugar residue. Nonlimiting examples are the nucleosides of formulas 29-38, derivatives of all four key nucleosides: thymidine, 2'-deoxycytidine, 2'-deoxyguanosine and 2'-deoxyadenosine, illustrated below.

The base is preferably a purine or pyrimidine base or its derivative, and preferably is thymine, uracil, 5-halouracil, cytosine, 5-halocytosine, adenine, guanine, 2,6-diaminopurine, 2-amino-6-chloropurine, 2-aminopurine, 5-alkyluracil, 5-alkylocytosine, 2-thiouracil, 2,4-dithiouracil or 4-thiouracil. Preferably the metallacarborane group contains a metal atom (Me) selected among Sn, Mn, Tc, Re, Fe, Ru, Os, Co, Rh, Ir, Ni, Pd, Pt, Cu, Ag, Au, Sc, Cr, Mg, Zr, Mo, Sm, Yb, Hf, W, Hg, Gd, U or Y or nonmetal selected among As, S, Si, Se, Te, P, Sb, Bi, Ge or N, or theirs isotopes. Preferably the metallacarborane group is attached to the nucleoside directly or through a linker according to the formula —[(CH$_2$)$_n$—(W)$_m$]$_k$— wherein n is 0-5, m is 0 or 1, k is 1-6, and W is O, S, S(O), S(O)$_2$, Se, NR (wherein R=H, alkyl, haloalkyl, alkoxyalkyl or aryl), X—P(Z)(Y)O (wherein X=O, S, Se; Z=O, S, Se; Y=OH, SH, SeH or alkyl, haloalkyl, alkoxyalkyl, aryl or halogen, specifically fluorine, also CH=CH, CC, N=N, CHOH and CHN$_3$

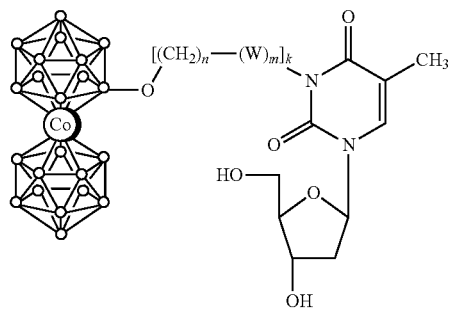

29

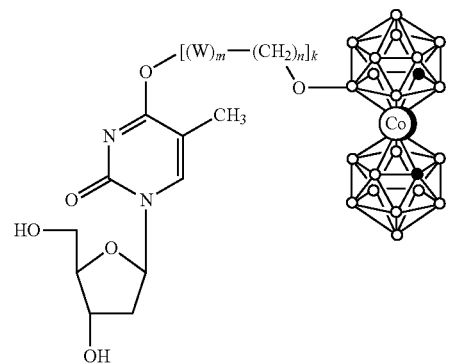

31

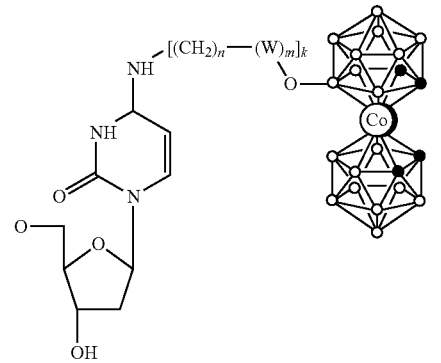

31

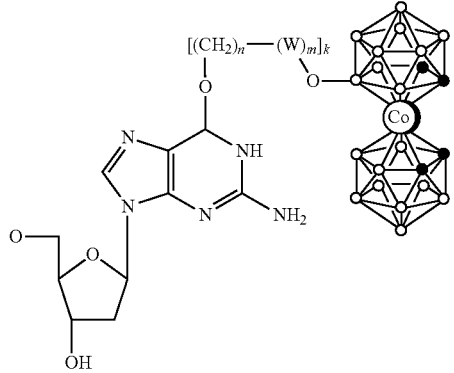

36

-continued

37
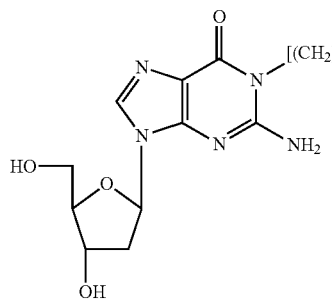

38
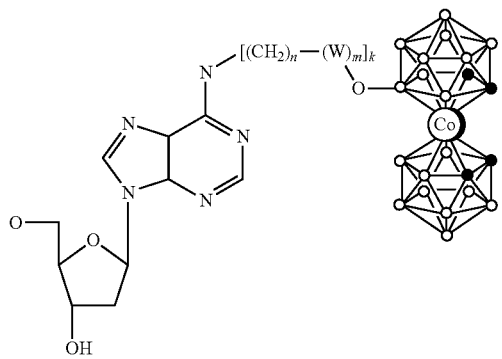

32
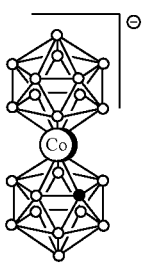

33
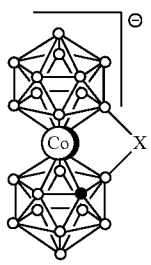

X = (CH₂)₃—
(CH₂)₅—
—CH₂OCH₂—
—CH₂SO₂CH₂—

34
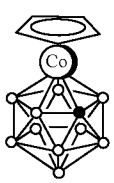

-continued

35
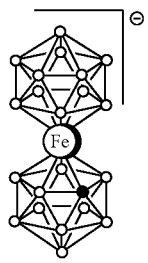

In one embodiment, a nucleoside derivative is provided that contains -{8-[(1,2-dicarba-closo-undecaboranyl)-3,3'-Me-(1',2'-dicarba-closo-undecaboranyl)atyl]} or -{8-[(1,2-dicarba-closo-undecaborano)-3-Me-cyclopentadienyl]ate} group. Preferably the metallacarborane group is a {(1,2-dicarba-closo-undecaboranyl)-3,3'-cobalt-(1',2'-dicarba-closo-undeca-boranyl)late} (COSAN) (32) or {[(1,2-dicarba-closo-undecaboranyl)-3-cobalt-cyclopentadienyl]atyl}(34). Nonlimiting examples are the metallacarborane groups of 32-35 illustrated above.

In one embodiment the pyrimidine nucleoside derivative provided in this invention contains -{diethylenoxy-{8-[(1,2-dicarba-closo-undecaboranyl)-3,3'-cobalt-(1',2'-di-carba-closo-undecaboranyl)anyl]} group preferably at position 2O,4O or 3N of thymine or 2O or 4N of cytosine. In another embodiment the purine nucleoside derivative provided in this invention contains -{diethylenoxy-{8-[(1,2-dicarba-closo-undecaboranyl)-3,3'-cobalt-(1',2'-di-carba-closo-undecaboranyl)anyl]} group preferably at position 1N, 2N or 6O of guanine or 6N of adenine. In another embodiment one or more hydroxyl functions (—OH) of the sugar residue is replaced by —OP(Z)(Y)X group, wherein: Z=O, S, Se; Y=OH, SH, SeH or alkyl, haloalkyl, alkoxyalkyl, aryl or halogene: X=OH, SH, SeH or alkyl, haloalkyl, alkoxyalkyl, aryl or halogene. In another embodiment one or more hydroxyl functions (—OH) of the sugar residue is replaced by —OP(Y)X group, wherein: Y=alkyl, haloalkyl, alkoxyalkyl (—O-alkyl), aryl, aryloxyaryl (—O-aryl), NR₂ or halogene; X=alkyl, haloalkyl, alkoxyalkyl (—O-alkyl), aryl, aryloxyaryl (—O-aryl), NR₂ or halogene. Also preferable the nucleoside derivative provided in this invention is a nucleotide, preferably nucleoside mono-, di- or triphospate. Preferably the free hydroxyl functions of the sugar residue of the natural or modified nucleoside as well as amino groups of the nucleic base are protected as known to those skilled in the art, allowing use of the nucleoside for the synthesis of DNA- or RNA-oligonucleotides.

In another embodiment the metallacarborane group is attached to a phosphorus atom of the nucleotide presented in this invention. Preferably the metallacarborane group is attached to the phosphorus atom directly or through a linker.

The subject of this invention is also compounds selected among the following nonlimiting examples: 5'-O-monomethoxytrityl-3'-O-acetyl-3-N-(diethyleneoxy-8-COSAN)-thymidine (24a), 5'-O-monomethoxytrityl-3'-O-acetyl-4-O-(diethyleneoxy-8-COSAN)-thymidine (24b), 4-O-(diethyleneoxy-8-COSAN)-thymidine (28b), 8-dioxane-O-COSAN (23), 5'-O-monomethoxytrityl-4-O-(diethyleneoxy-8-COSAN)-thymidine (25a), 5'-O-monomethoxytrityl-3'-O-(N,N-diisopropyl-beta-cyanoethyl)4-O-(diethyleneoxy-8-COSAN)thymidine amidophosphonate (26), wherein COSAN is [(1,2-dicarba-closo-undecaboranyl)-3,3'-cobalt-(1',2'-dicarba-closo-undecaboranyl)]atyl. The subject of the invention is also compounds 36-38 being nucleosides containing metallacarborane including cytosine, adenine or guanine.

The nucleosides containing a metallacarborane group presented in this invention are natural nucleosides such as thymidine, deoxycytidine, deoxyadenosine, deoxyguanosine or theirs counterparts in ribo-series, or synthetic analogues of nucleosides modified within the nucleic base or sugar residue such as L-nucleosides, carbocyclic nucleosides, acyclic nucleosides, and others. The above mentioned nucleoside analogues are examples only and do not limit the subject of the present invention. The metallacarboranes group can contain at least one or more metal ions or nonmetal atom.

According to another aspect of the invention, an oligonucleotide is provided that contains at least one metallacarborane complex attached to a nucleic base, sugar residue or internucleotide linkage or analogue of sugar residue. Preferably the metallacarborane modification is attached to the 3'-terminal nucleoside unit, also preferably it is attached to the 5'-terminal unit, at 5'-end of the oligonucleotide chain or its middle location.

Preferably the metallacarborane group contains a metal atom (Me) selected among Sn, Mn, Tc, Re, Fe, Ru, Os, Co, Rh, Ir, Ni, Pd, Pt, Cu, Ag, Au, Sc, Cr, Mg, Zr, Mo, Sm, Yb, Hf, W, Mg, Gd, U or Y or nonmetal selected among As, S, Si, Se, Te, P, Sb, Bi, Ge or N, or their isotopes. Preferably the metallacarborane group is attached to the nucleoside directly or through a linker according to the formula —[(CH$_2$)$_n$—(W)$_m$]$_k$— wherein n is 0-5, m is 0 or 1, k is 1-6, and W is O, S, S(O), S(O)$_2$, Se, NR (wherein R=H, alkyl, haloalkyl, alkoxyalkyl or aryl), X—P(Z)(Y)O (wherein X=O, S. Se; Z=O, S, Se; Y=OH, SH, SeH or alkyl, haloalkyl, alkoxyalkyl, aryl or halogen, specifically fluorine, also CH=CH, CC, N=N, CHOH and CHN$_3$.

Preferably the metallacarborane modified oligonucleotide can hybridize in vitro and/or in vivo to complementary DNA or RNA forming double stranded structures, it can also preferably hybridize in vivo to double stranded DNA.

In one embodiment, an oligonucleotide is provided that contains -{8-[(1,2-dicarba-closo-undecaboranyl)-3,3'-Me-(1',2'-dicarba-closo-undeca-boranyl)atyl]} or -{8-[(1,2-dicarba-closo-undecaborano)-3-Me-cyclopentadienyl]atyl} group. Preferably the metallacarborane group is a -{8-[(1,2-dicarba-closo-undecaboranyl)-3,3'-cobalt-(1',2'-dicarba-closo-undecaboranyl)atyl]} or -{8-[(1,2-dicarba-closo-undecaboranyl)-3-cobalt-cyclopentadienyl]atyl}.

Preferably the modified oligonucleotide provided in this invention contains -{diethyleneoxy-{8-[(1,2-dicarba-closo-undecaboranyl)-3,3'-cobalt-(1',2'-dicarba-closo-undecaboranyl)atyl]} group preferably at position 20, 40 or 3N. Preferably the modifying metallacarborane moiety is attached at position 3N— or 4O— of thymidine ($^{BCCo}$T).

In one embodiment the modified oligonucleotide is 5'-d($^{BCCo}$TGCTGGTTTGGCTG)-3'(SEQ ID NO:1). This example is merely illustrative, and not intended to limit the scope of the invention.

The oligonucleotides containing metallacarborane group presented in this invention are natural nucleic acids type of DNA or RNA as well as oligonucleotides modified within nucleic base, sugar residue and internucleotide linkage. The unlimiting examples of these oligonucleotides are phosphorothioate, methylphosphonate and peptide (PNA) oligomers containing at least one modification within the oligonucleotide chain.

According to another aspect of the present invention, a novel method is provided for the preparation of a nucleoside derivative, particularly an oligonucleotide, containing a metallacarborane group. The disclosed method for the synthesis of the nucleoside/metallacarborane conjugate is based on the use of a suitably protected nucleoside or its analogue containing at least one carbonyl group able to participate in a keto-imine equilibrium and/or amine or hydroxyl group in the nucleic base. The nucleoside is then activated in the reaction with a proper activator, an inorganic base such as sodium hydride, sodium aluminum hydride, potassium tert-butoxide or an organic base and treated with 8-dioxanyl-{8-[(1,2-di-carba-closo-undecaboranyl)-3,3'-Me-(1',2'-dicarba-closo-undecaboranyl)atyl]} or 8-tetrahydrofuranyl-, or 8-tetrahydropyranyl-{8-[(1,2-dicarba-closo-undecaboranyl)-3,3'-Me-(1',2'-di-carba-closo-undecaboranyl)atyl]}. The reaction medium is a hydrocarbon or its derivative characterized by the melting point from minus 100 up to plus 150 Celsius degrees such as xylenes, mesitylene, hexamethylbenzene or naphthalene. The desired product is isolated and the 2', 3' and 5'-hydroxyl groups are deprotected into free hydroxyl (—OH) functions as desired (Example 1, 2).

The subject of this invention is the application of the carboranes and metallacarborane according to the invention, as defined above, as a label for nucleosides, nucleotides, oligonucleotides, proteins, antibodies and other biological compounds and their derivatives.

Preferably the carborane and metallacarborane labels provided in this invention are detected by electrochemical methods. Preferably the compounds labelled with the carborane or metallacarborane group are oligonucleotides or their derivatives.

Preferably the oligonucleotides labelled as described in this invention will be used as hybridization probes.

According to another aspect of the present invention, oligonucleotides containing carborane or metallacarborane groups will be used as a material for nanoconstruction, construction of DNA microarrays and biosensors, especially electrochemical biosensors. Preferably compounds described in this invention are used for detecting elements immobilized on the electrode surface.

The subject of this invention is also the application of the modified nucleotide according to the invention containing carborane and/or metallacarborane group, or its derivative, as defined above, in the methods of electrochemical detection. Preferably the derivative of the nucleotide is an oligonucleotide. In one embodiment the compounds described in the present invention are nucleosides, therefore also nucleotides and oligonucleotides labelled with carborane group. Compounds of this kind, and methods of their synthesis are described in the documents referred to in the description of the background of the invention, namely U.S. Pat. No. 6,180,766.

In the present invention an entirely new class of metallated nucleoside and nucleotide conjugates containing metallacarborane cage is provided, also oligonucleotides containing metallacarborane modification are proposed. The nucleoside can contain purine as well as pyrimidine nucleic base, and be natural or a modified entity. The provided nucleoside conjugates contain metal in the form of a metallacarborane complex and consist from two up to eighteen times more boron than was available so far. Because of unique properties of boron clusters they form complexes with a broad range of metals such as Sn, Mn, Tc, Re, Fe, Ru, Os, Co, Rh, Ir, Ni, Pd, Pt, Cu, Ag, Au, Sc, Cr, Mg, Zr, Mo, Sm, Yb, Hf, W, Hg, Gd, U or Y and others and can include several nonmetals such as As, S, Si, Se, Te, P, Sb, Bi, Ge or N and theirs isotopes. (Grimes, 1995; Hall i inni, 2000; Hosmane i Maguire, 1987; Housecroft, 1990; Saxena i Hosmane, 1993).

Provided in the present invention are nucleosides, nucleotides and oligonucleotides containing metallacarborane cage that can be applied as among others as: modified primers in amplification of RNA and DNA, drugs, boron carriers for BNCT (boron neutron capture therapy), radiopharmaceuticals bearing a range of isotopes useful in different types of radiotherapy, molecular probes, elements of biosensors, materials for nanotechnology and others.

In contrast to the sandwich type compounds such as ferrocene, the number of metallacarborane of different structures, containing various metals is very high. The electrochemical properties of many metallacarborane complexes are known. The chemical nature of the new class of label provided in this invention makes possible incorporation into the label a molecule of different metals such as Sn, Mn, Tc, Re, Fe, Ru, Os, Co, Rh, Ir, Ni, Pd, Pt, Cu, Ag, Au, Y and others. This property increases dramatically the range of potential practical applications of the oligonucleotides containing metallacarborane label. Because of a great diversity of metals which can be included into the metallacarborane structure and a broad range of redox potentials characteristic for these metals, it may be expected that the oligonucleotide probes labelled with different a metallacarborane can be detected selectively in the mixture. This in turn, may be of importance for potential applications of metallacarborane labeled oligonucleotides in such technologies as nanotechnology, DNA-chips or DNA sensors.

BRIEF DESCRIPTION OF THE FIGURES

For the better presentation of the substance of this invention and enable its implementation the text of the application is supplemented with figures.

DETAILED DESCRIPTION OF THE INVENTION

Figure 1:
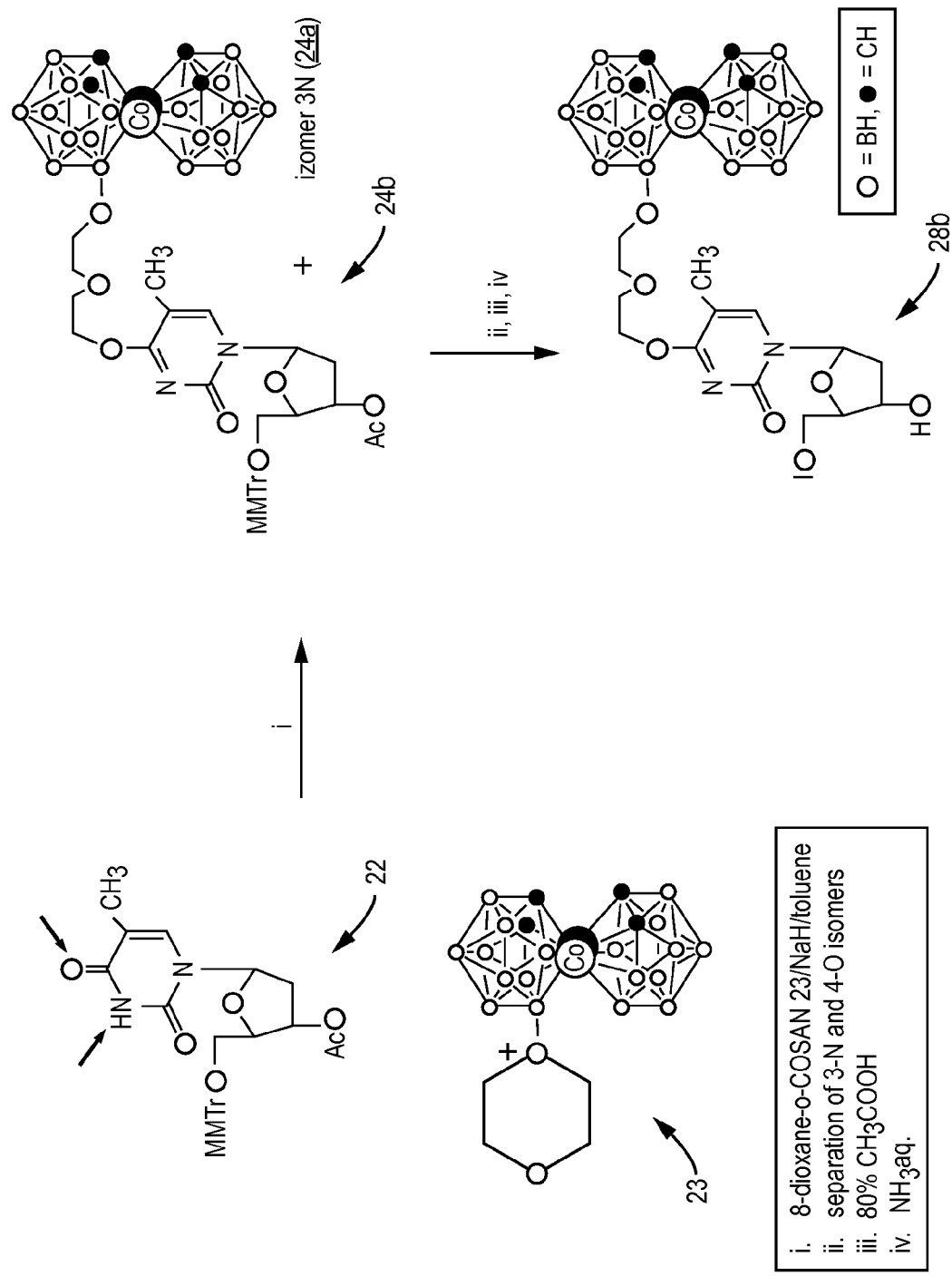
FIG. 1. Synthesis of 5'-O-monomethoxytrityl-3'-O-acetyl-3-N-(diethylenoxy-8-COSAN)-thymidine (24a), 5'-O-monomethoxytrityl-3'-O-acetyl-4-0-(diethylenoxy-8-COSAN)-thymidine (24b) and 4-O-(diethylenoxy-8-COSAN)-thymidine (28b), wherein COSAN is [(1,2-dicarba-closo-undecaboranyl)-3,3'-cobalt-(1',2'-dicarba-closo-undecaboranyl)]atyl.

The term alkyl, as used herein, unless otherwise specified, refers to a saturated straight, branched, or cyclic, primary, secondary, or tertiary hydrocarbon of C1 to C10, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a C1 to C4 saturated straight or branched alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, N6-alkypurines, N6-acylpurines (wherein acyl is C(O) (alkyl, aryl, alkylaryl, or arylalkyl), N6-benzylpurine, N6-halopurine, N6-vinylpurine, N6-acetylenic purine, N6-acyl purine, N6-hydroxyalkyl purine, N6-thioalkyl purine, N2-alkylpurines, N2-alkyl-6-thiopurines, thymine, cytosine, 6-azapyrimidine, 2- and/or 4-thiopyrmidine, uracil, C5-alkylpyrimidines, C5-benzylpyrimidines, C5-halopyrimidines, C5-vinlypyrimidine, C5-acetylenic pyrimidine, C5-acyl pyrimidine, C5-hydroxyalkyl purine, C5 amidopyrimidine, C5-cyanopyrimidine, C5-nitropyrimidine, C5-aminopyrimidine, N2-alkylpurines, N2-alkyl-6-thipourines, 5-azacylidinyl, 5-azauracilyl, triazolopyridinyl, imidazolopyridinyl, pyrrolopyrimidinyl, pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methylsulfonyl, and p-toluoylsulfonyl.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methylsulfonyl, and p-toluoylsulfonyl.

The term alkenyl, as referred to herein, and unless otherwise specified, refers to a straight, branched, hydrocarbon of C2 to C10 with at least one double bond.

The term acyl refers to moiety of the formula —C(O)R', wherein R' is alkyl; alkoxyalkyl including methoxymethyl; arylalkyl including benzyl; aryloxyalkyl such as phenoxymethyl; aryl including phenyl optionally substituted with halogen, C1 to C4 alkyl or C1 to C4 alkoxy, or the residue of an amino acid.

The term oligonucleotide refers to an oligomer of thirty-five or less nucleotides linked through the 3' and 5'-hydroxyl or 2'- and 5'-hydroxyl groups.

The term "metallacarboranes", as used herein, refers to compounds of metallocene type complexes consisting at least one carborane cage ligand and one or more metal atoms. For a review of metallacarborane chemistry see Grimes, R. N., 2000. Metallacarboranes in the new millennium, Coord. Chem. Rev., 200-202, 773-811; Saxena, A. K., Hosmane, N. S., 1993.

Recent advances in the chemistry of carborane metal complexes incorporating d- and f-block elements. Chem. Rev., 93, 1081-1124; Grimes, R. N., Transition Metal Metallacarboranes in Comprehensive Organometallic Chemistry, 1995, vol. I, Housecroft C. E., ed., Pergamon, N.Y., 373-430.

Derivative (of the nucleoside, nucleotide, oligonucleotide, protein, antibodies and other biological molecules) is a chemically or physically changed form of the mother molecule (substrate). DNA hybridization technology—the technologies and their applications based on specific formation of a double stranded nucleic acid structure due to specific nucleic bases recognition according to Watson-Crick rule.

DNA microarrays—terminologies that have been used in the literature to describe this technology include, but not limited to: biochip, DNA chip, DNA microarray, and gene array. Affymetrix Inc. owns a registered trademark, GeneChip®, which refers to its high density, oligonucleotide-based DNA arrays. However, in some articles that appeared in professional journals, popular magazines, and the world wide web the term "gene chip(s)" has been used as a general terminology that refers to the microarray technology. Base-pairing (i.e., A-T and G-C for DNA; A-U and G-C for RNA) or hybridization is the underlining principle of DNA microarray. An array is an orderly arrangement of samples. It provides a medium for matching known and unknown DNA samples based on base-pairing rules and automating the process of identifying the unknowns. In general, arrays are described as macroarrays or microarrays, the difference being the size of the sample spots. Macroarrays contain sample spot sizes of about 300 microns or larger and can be easily imaged by existing gel and blot scanners. The sample spot sizes in microarray are typically less than 200 microns in diameter and these arrays usually contain thousands of spots.

A DNA sensor, is an immobilized DNA recognition element (receptor) coupled to a transducer unit and an electronic amplifier. Dependent on the kind of interaction between the substrate (S) and the receptor (R) the entities may differ: Affinity sensors (affinity to the substrate; S+R "<-->" RS), metabolism sensors (use of the substrate; S+R "<-->" RS "<-->" P+R).

Electrochemical DNA sensors, the device detecting the hybridization process between the target nucleic acid and the nucleic acid probe. The DNA sensor comprises a nucleic acid recognition layer and a signal transducer. The signal transducer determines that the hybridization occurred on the base of the electrochemical process triggered by the hybridization and converts this into an electronic signal.

Nanotechnology, the development and use of devices that have a size of only a few nanometers. Research has been carried out into very small components, many of which depend on quantum effects and may involve movement of a very small number of electrons in their action. Such devices would act faster than larger components. Considerable interest has been shown in the production of structures on a molecular level by suitable sequences of chemical reactions or lithographic techniques. It is also possible to microscopically manipulate individual atoms on surfaces using a variant of the atomic force, for example, high density data storage devices.

Nucleoside is defined as a compound consisting a five-carbon sugar molecule (a pentose, ribose or deoxyribose) and an organic base, purine or pyrimidine.

Nucleotide is defined as a nucleoside consisting of a phosphate group.

Example 1

5'-O-Monomethoxytrityl-3'-O-acetyl-3-N-(diethyleneoxy-8-COSAN)thymidine (24a) and 5'-O-monomethoxytrityl-3'-O-acetyl-4-O-(diethyleneoxy-8-COSAN)thymidine (24b) (FIG. 1), wherein COSAN is [(1,2-dicarba-closo-undecaboranyl)-3,3'-cobalt-(1',2'-dicarba-closo-undecaboranyl)]atyl.

The procedure was performed under positive pressure of argon. 5'-O-monomethoxytrityl-3'-O-acetylthymidine (22) (0.9 g, 1.6 mmol) and 8-dioxane-COSAN (2, 1.4 g, 3.3 mmol) were mixed together then dried under high vacuum over $P_2O_5$ for 24 h, next NaH (60% suspension in mineral oil, 80 mg, 3.3 mmole) was added followed by anhydrous toluene (18 mL). The reaction mixture was stirred at 70° C. in an oil bath. After 8 h an excess of NaH was removed by centrifugation and supernatant was added dropwise into hexane (135 mL). The resultant precipitate was separated by centrifugation and the sediment was dried under vacuum yielding 2.4 g of crude 24 as a mixture of 3-N and 4-O isomers (24a and 24b, respectively). Crude 24 was purified by silica gel column chromatography (70 g silica gel, 230-400 mesh) using 12% $CH_3OH$ in $CHCl_3$, containing 1% $Et_3N$ as the eluting solvent system. The yield of 24a was 221 mg and 24b was 450 mg. 24a: TLC ($CH_3CN/CHCl_3$, 1:2): $R_f$ 0.14; UV ($CH_3CN$): $\lambda_{min}$ 227.46, 249.18, 287.30 nm, $\lambda_{min}$ 234.43, 261.89, 313.93 nm; $^1$H-NMR ($C_6D_6$): 1.8-3.5 (bm, 21H, BH-COSAN), 1.58 (s, 3H, $CH_3CO$), 1.71 (s, 3H, $CH_3$-5), 2.54 (m, 2H-2'), 2.95-

3.08 (m, 4H, 4×CH—COSAN), 3.28-3.41 (bs, 4H, 2×OCH$_2$), 3.43 (s, 3H, CH$_3$O), 3.46-3.52 (q, 2H-5',5"), 3.92 (bs, 2H, OCH$_2$), 3.96 (s, 1H-4'), 4.48-4.59 (m, 2H, OCH$_2$), 5.36 (s, 1H-3'), 6.31 (s, —H arom. in 4-CH1H-1'), 6.87 (d, 2H, $_3$OPh), 7.28-7.60 (m, 12H, H arom. in MMTr), 8.11 (s, 1H-6); $^{13}$C-NMR (C$_6$D$_6$): 13.62 (CH$_3$-5), 20.99 (CH$_3$ in CH$_3$CO), 39.76 (C-2'), 48.10, 51.94 (C-COSAN), 55.72 (CH$_3$O), 64.61 (C-5'), 68.73, 73.48 (OCH$_2$), 75.67 (C-3'), 86.41 (C-4'), 87.46 (C-1'), 88.74 (C-methylidene in MMTr), 114.65, 129.23, 131.40, 144.85, 145.06 (MMTr), 135.92-C in 4-CH(C-6), 156.91 (C-2), 160.24 ($_3$OPh), 170.30 (CO in CH$_3$CO), 176.38 (C-4); $_{11}$B-NMR (C$_6$D$_6$); 30.50-32.00 (bs, 18B); FAB-MS (-VE, NBA) 966.9 [M−1]. 24b: TLC (CH$_3$CN/CHCl$_3$, 1:2): R$_f$ 0.41; UV (CH$_3$CN): $\lambda_{min}$ 252.87 nm, $\lambda_{max}$ 283.91 nm, 311.84 nm; $^1$H-NMR (C$_6$D$_6$): 1.50-4.00 (bm, 21H, BH-COSAN), 1.48 (s, 3H, CH$_3$-5), 1.62 (s, 3H, CH$_3$CO), 2.55 (m, 2H-2'), 2.77-3.07 (m, 4H, 4×CH—COSAN), 3.21 (bs, 4H, 2×OCH$_2$), 3.37 (s, 3H, CH$_3$O), 3.45-3.51 (q, 2H-5', 5", J$_{5'5''}$=9.04), 3.88 (bs, 2H, OCH$_2$), 4.08 (s, 1H-4'), 4.37-4.43 (m, 2H, OCH$_2$), 5.43 (s, 1H-3'), 6.64 (s, —H arom. in CH1H-1'), 6.82 (d, 2H, $_3$OPh), 7.06-7.52 (m, 12H, H arom. in MMTr), 8.20 (s, 1H-6); $^{13}$C-NMR (C$_6$D$_6$): 12.33 (CH$_{3-5}$), 21.09 (CH$_3$-acetyl), 40.22 (C-2'), 48.12, 51.85, 51.95 (C-COSAN), 55.60 (CH$_3$O), 64.43 (C-5'), 68.27, 71.68, 73.26 (OCH$_2$), 75.53 (C-3'), 85.97 (C-4'), 87.75 (C-1'), 88.56 (C-methylidene in MMTr), 114.55, 129.14, 129.23, 129.55, 131.41, 142.33, 144.94, 145.09 (MMTr), 135.95 (C-6), 158.93 (C-2), 160.21 (C-4 in 4-CH$_3$OPh), 170.58 (C-4), 172.52 (CH$_3$-acetyl); $^{11}$B-NMR (C$_6$D$_6$): 30.50-32.00 (bs, 18B); FAB-MS (-VE, NBA) 966.9 [M−1].

Analogously other metallacarboranes can be incorporated into purine or pyrimidine nucleic base and sugar residue of the nucleoside unit.

Example 2

4-O-(diethylentoxy-8-COSAN)thymidine (28) (FIG. 1). 5'-O-Monomethoxytrityl-4-O-(diethyleneoxy-8-COSAN)thymidine (25a)

(0.1 g, 0.11 mmol) was dissolved in CH$_3$CN (5 mL) then to the resultant solution acetic acid was added (80% CH$_3$COOH, 10 mL). After 2.5 h at room temperature the reaction went to the completion (TLC control, solvent system CHCl$_3$/CH$_3$OH, 8:2) and the solvents were evaporated under reduced pressure yielding crude 28 (0.18 g). Crude 28 was purified by silica gel column chromatography (2 g of silica gel, 230-400 mesh) using 30% CH$_3$OH in CHCl$_3$ as eluting solvent system. The yield of 28 was 40 mg (58%). TLC (CHCl$_3$/CH$_3$OH, 8:2): R$_f$ 0.18; UV (CH$_3$CN): $\lambda_{min}$ 237.93, $\lambda_{max}$ 282.76, $\lambda_{max}$ 310.67; $^1$H-NMR (CD$_3$OD): 1.2-3.2 (bm, 21H, BH-COSAN), 2.02 (s, 3H, CH$_3$-5), 2.16-2.21 (m 1H-2'), 2.40-2.44 (m, 1H-2"), 3.60-3.65 (m, 4H, 2×OCH2), 3.73-3.76 (dd, 1H-5'), 3.82-3.85 (m, 3H, 1H-5" and OCH$_2$), 3.96 (q, 1H-4'), 4.13 (s, 2H, 2×CH—COSAN), 4.38-4.39 (m, 1H-3'), 4.42-4.46 (m, 1H, OCH$_2$), 4.52-4.56 (m, 1H, OCH$_2$), 6.26 (t, 1H-1', J$_{1'2'}$=6.36), 8.13 (s, 1H-6); $^{13}$C-NMR (CD$_3$OD): 12.40 (CH$_3$-5), 42.24 (C-2'), 48.04 (C-COSAN), 55.15 (C-COSAN), 62.54 (C-5'), 68.13 (OCH$_2$), 69.83 (OCH$_2$), 69.98 (OCH$_2$), 71.69 (C-3'), 73.07 (OCH$_2$), 87.97 (C-1'), 89.11 (C-4'), 142.08 (C-6), 158.20 (C-2), 172.16 (C-4); $^{11}$B-NMR (CD$_3$OD, H-decoupled): 28.54 (s), 10.30 (s), 6.33 (s), 3.48 (s), 1.32 (s), from −1.59 to −2.19 (d), −11.47 (s), −14.68 (s); FAB-MS (-VE, NBA) 652.6 [M−1].

Method for the automated production of oligonucleotides are described below (Example 3 and 4). Given the disclosure herein, one of ordinary skill in the art will know how to prepare a wide variety of oligonucleotides with metallacarborane-containing nucleotide monomers for a diverse range of applications, all of which are intended to fall within the scope of this invention.

Example 3

Figure 2:
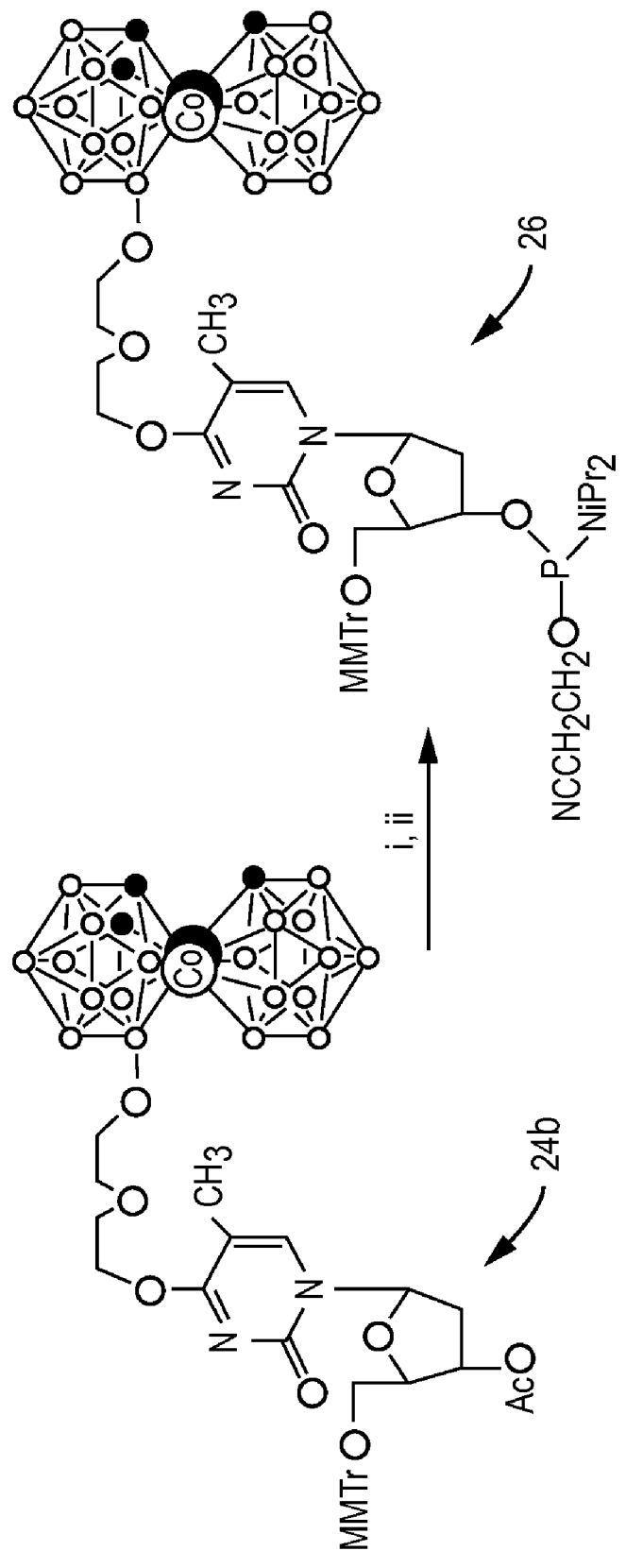
FIG. 2. Synthesis of modified monomer for oligonucleotide preparation: 5'-O-monomethoxytrityl-4-O-(diethylenoxy-8-COSAN)thymidine 3'-O-(N,N-diisopropyl-beta-cyanoethyl)amidophosphonate (26).
Figure 3:
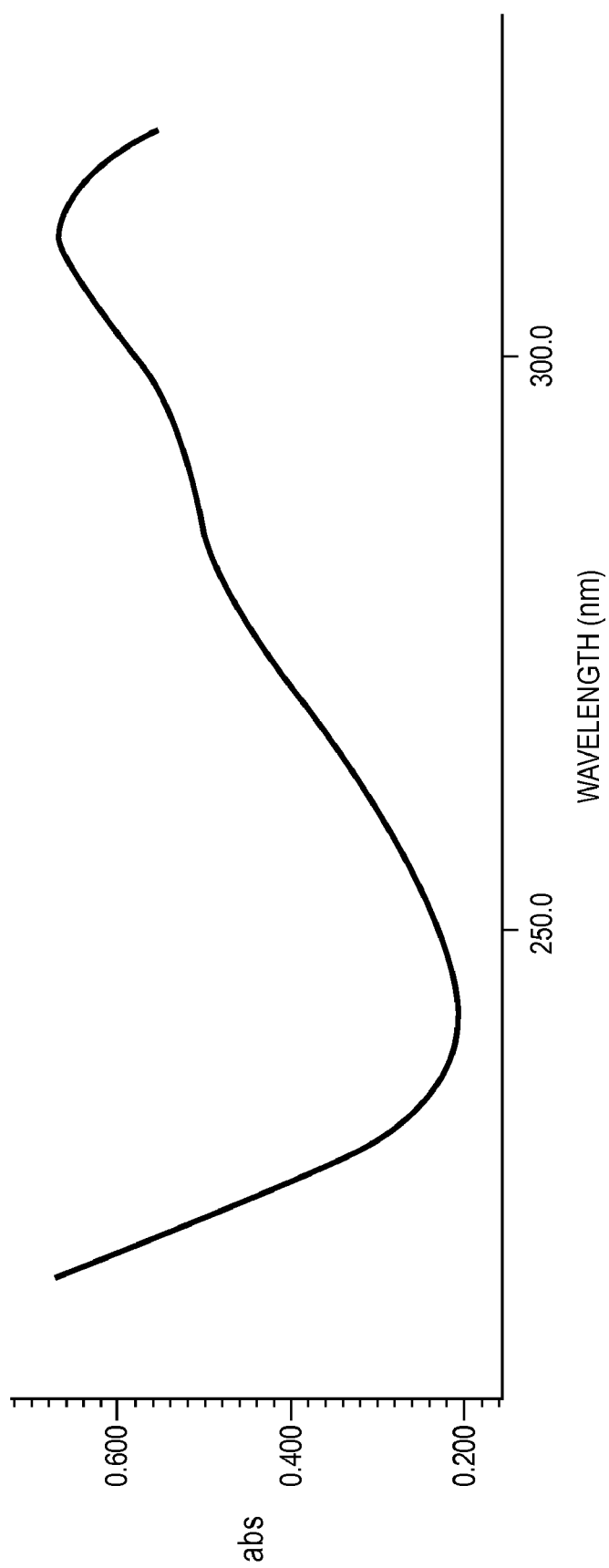
FIG. 3. UV spectrum of 4-O-(diethylenoxy-8-COSAN) thymidine (28b).
Figure 4:
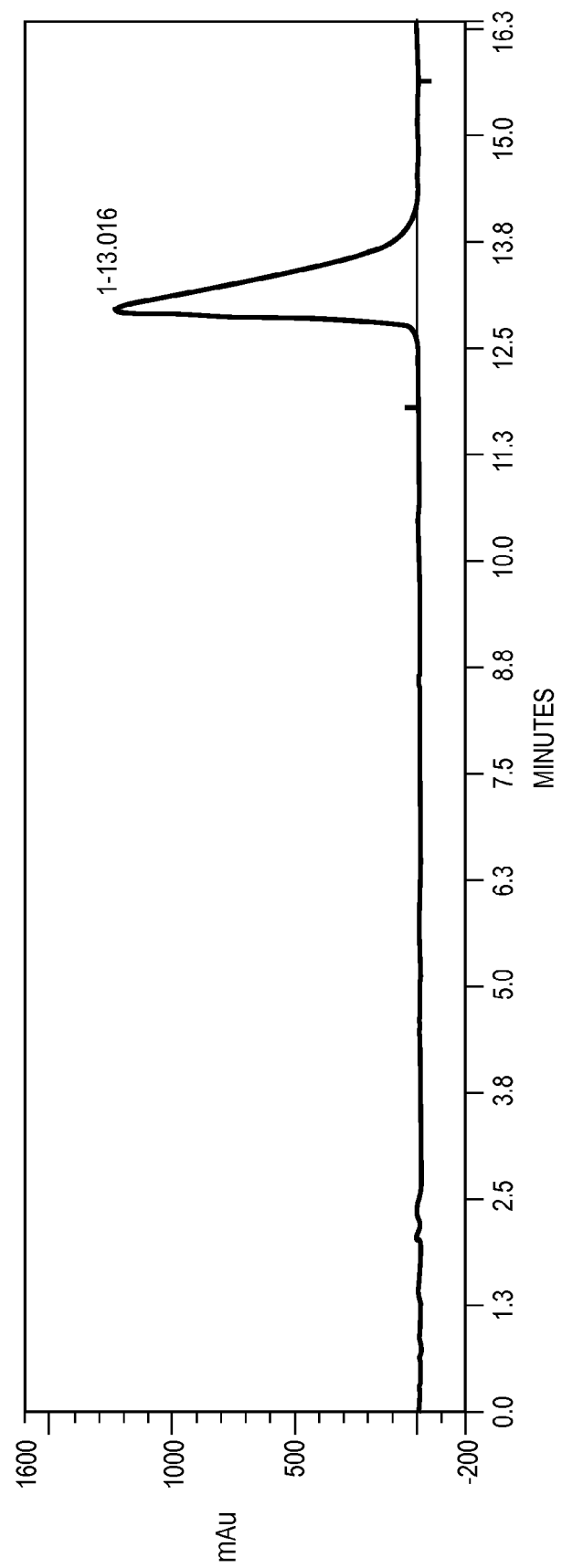
FIG. 4. RP-HPLC trace of 4-O-(diethylenoxy-8-COSAN) thymidine (28b).
Figure 5:
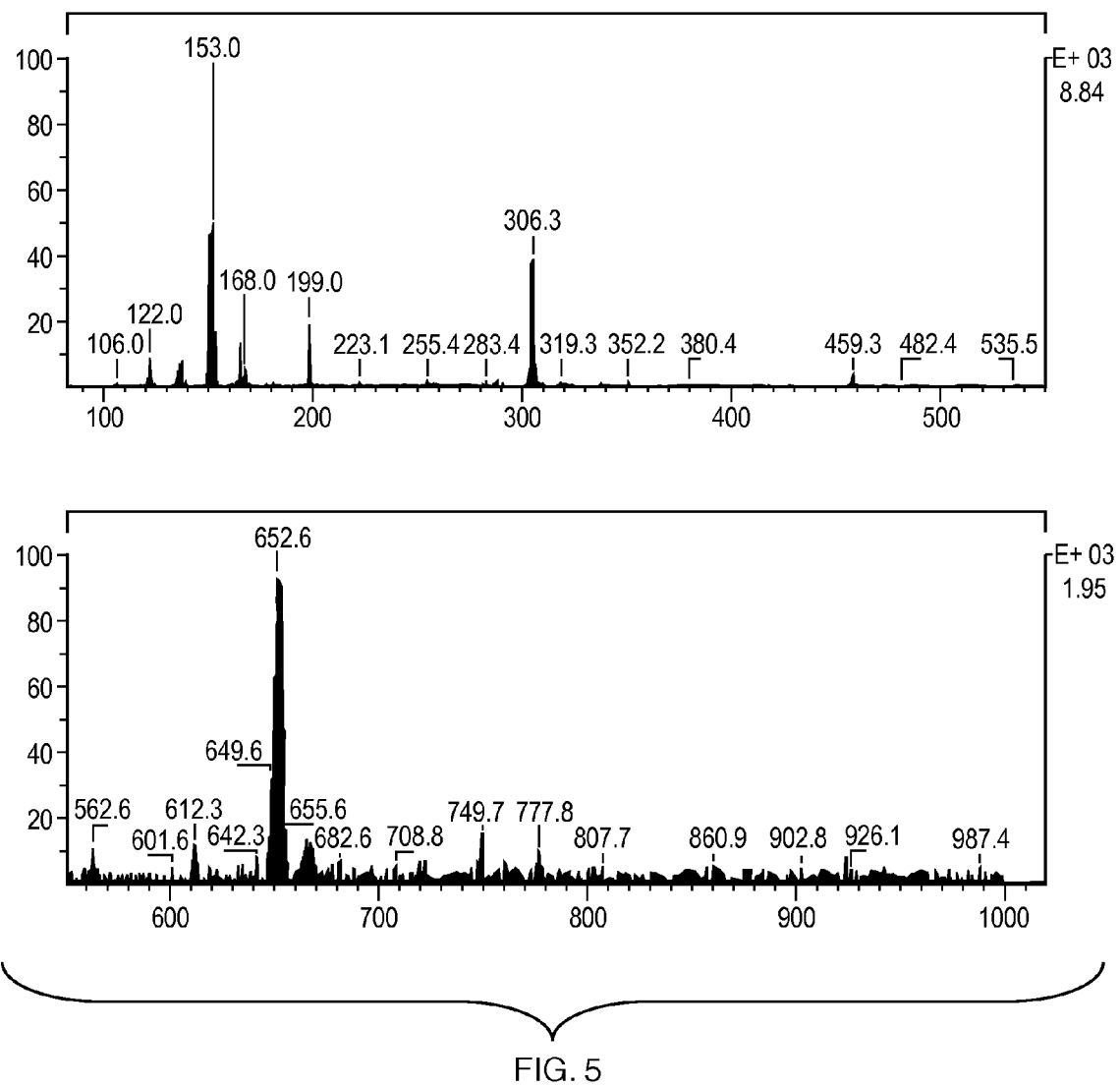
FIG. 5. Mass spectrum (FAB) of 4-O-(diethylenoxy-8-COSAN) thymidine (28b).
Figure 6:
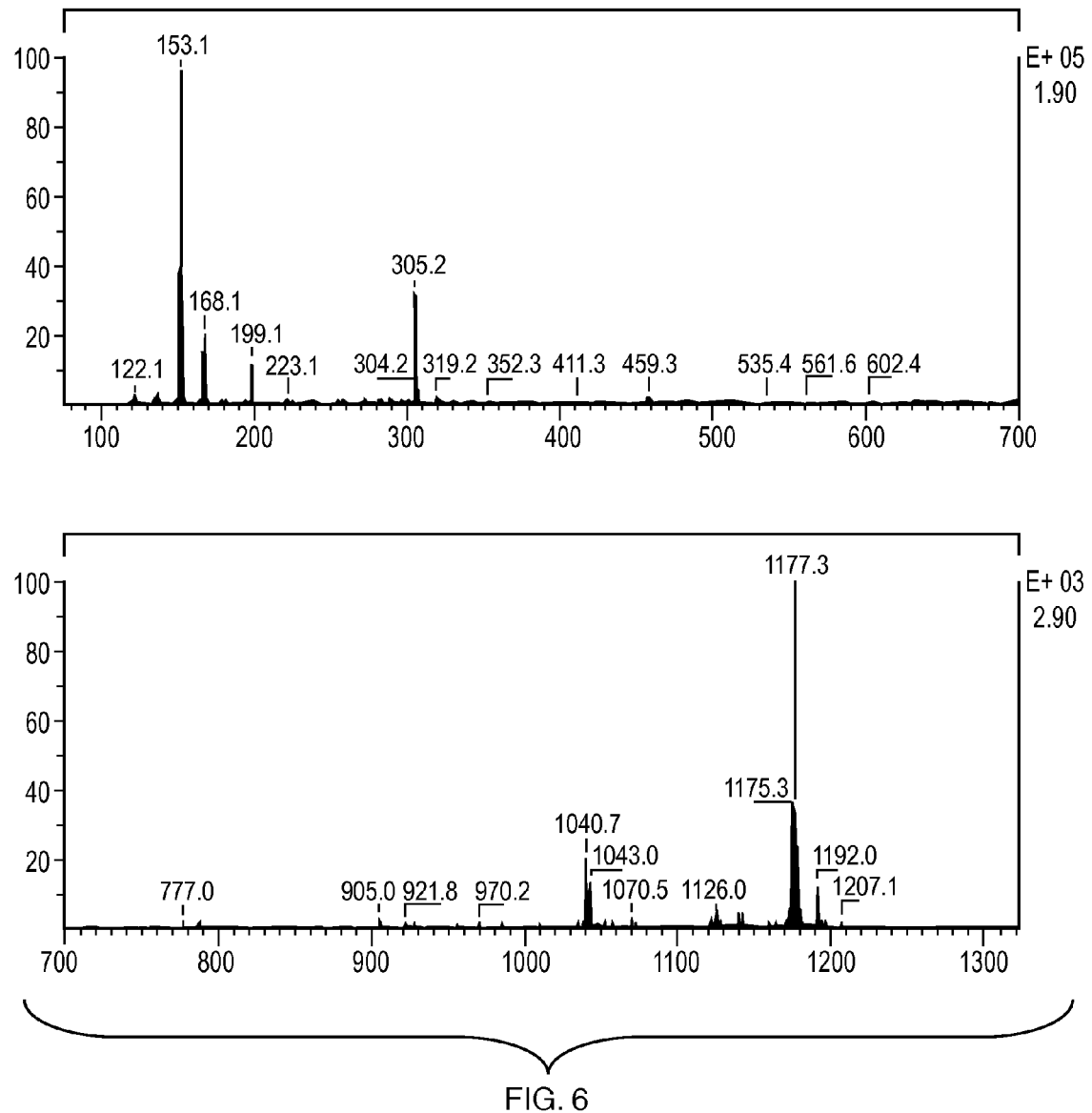
FIG. 6. Mass-spectrum (FAB) of 5'-O-monomethoxytrityl-4-O-(diethylenoxy-8-COSAN)thymidine 3'-O-(N,N-diisopropyl-beta-cyanoethyl)amidophosphonate (26).

5'-O-Monomethoxytrityl-4-O-(diethyleneoxy-8-COSAN)thymidine 3'-O—(N,N-diiso-propyl-2-cyanoethyl)phosphoramidite (26) (FIG. 2).

All procedures were performed under positive pressure of argon. 5'-O-Monomethoxytrityl-4-O-(bisethoxy-8-COSAN)thymidine (25a) (0.1 g, 0.11 mmol) was dried under high vacuum over P$_{20}$s for not less than 12 h, then was dissolved in CH$_2$Cl$_2$ (fresh distilled over CaH$_2$, 1.3 mL) and next N,N-diisopropylethylamine (0.075 mL) was added. To the resultant solution 2-cyanoethyl-N,N-diisopropylchlorophosphoramidite was added dropwise (0.072 mL, 0.32 mmole). After 4 h the reaction mixture was washed with H$_2$O (3×5 mL) then the organic layer was dried over MgSO$_4$ and solvent evaporated. The crude product 7 was obtained as colorless oil (0.11 g). Crude 7 was purified by silica gel column chromatography (6 g of silica gel, 230-400 mesh) using CH$_3$CN/CH$_2$Cl$_2$ (1:3) as eluting solvent system. The yield of 7 was 78 mg (65%). TLC (CH$_3$CN/CH$_2$Cl$_2$, 1:3): R$_f$ 0.25, UV (anhydrous CH$_3$CN): $\lambda_{min}$ 255.2 nm, $\lambda_{ma}$x 281.6 nm, $\lambda_{max}$ 311.3 nm; $^{31}$P-NMR (C$_6$D$_6$): 149.00 and 149.82 (1:1), FAB-MS [-VE, NBA] 1177 [M+2×Na]

Example 4

Figure 7:
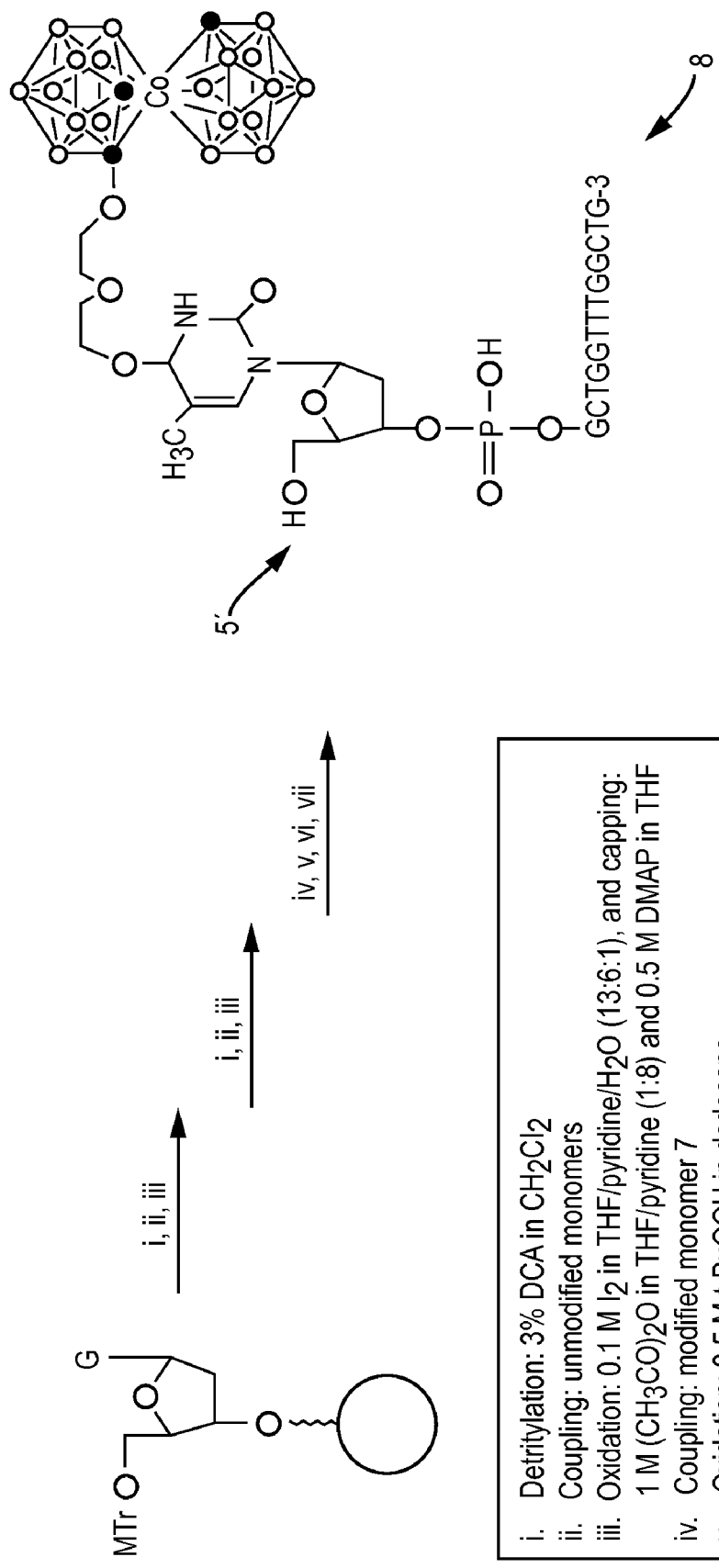
FIG. 7. Synthesis of tetradecanucleotide 5'-d($^{BEC}$TGCTG-GTTTGGCTG)-3'(SEQ ID NO:2) (27) complementary to the fragment of cytomegalovirus (HCMV) genome containing 4-O-(diethylenoxy-8-COSAN) thymidine (28b).
Figure 8:
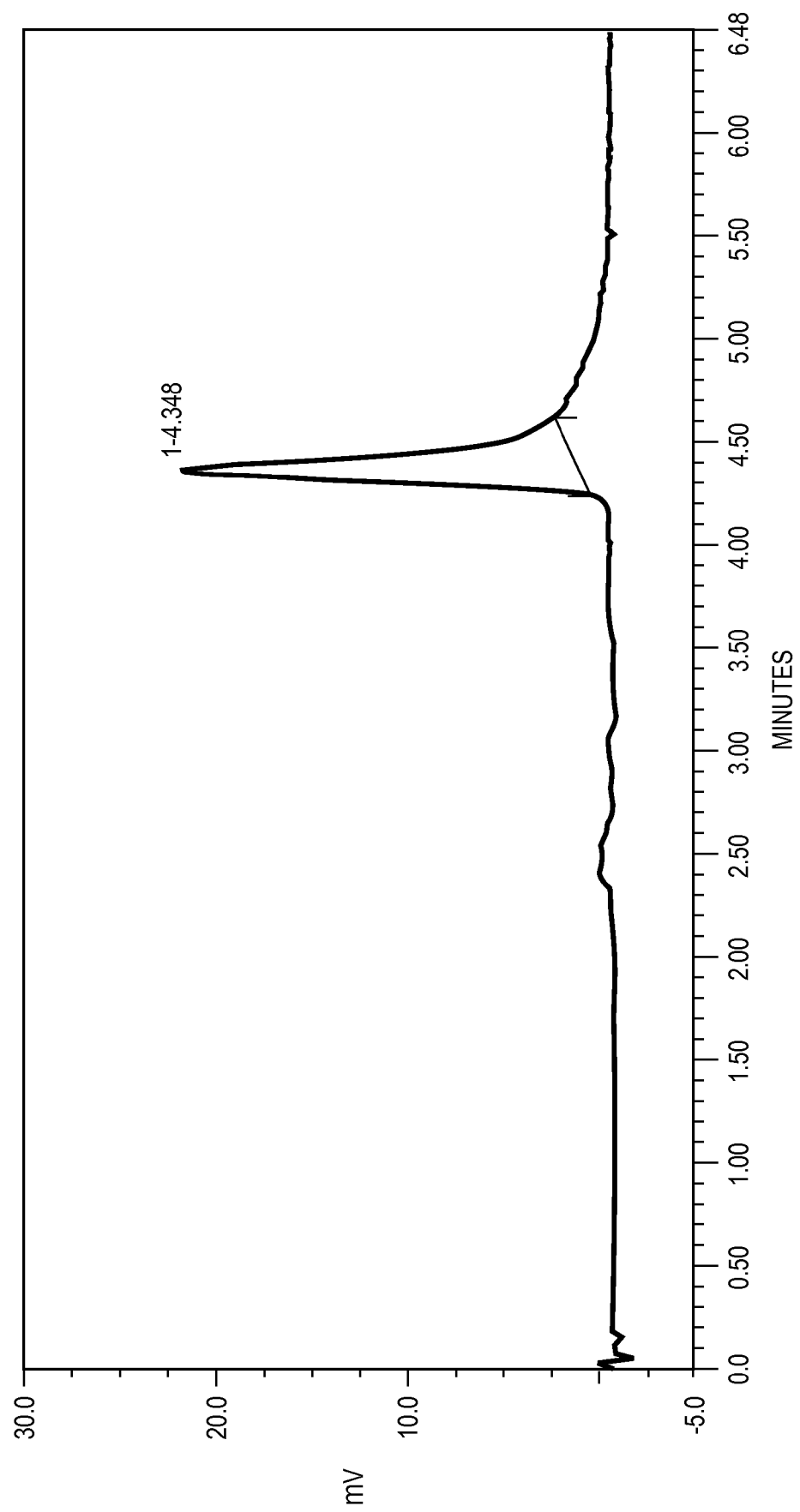
FIG. 8. RP-HPLC trace for 2'-O-[nido-(o-carboran-1-yl)] methyluridine (31) ($R_t$=4.6 min), electrochemical detection at +600 mV.
Figure 9:
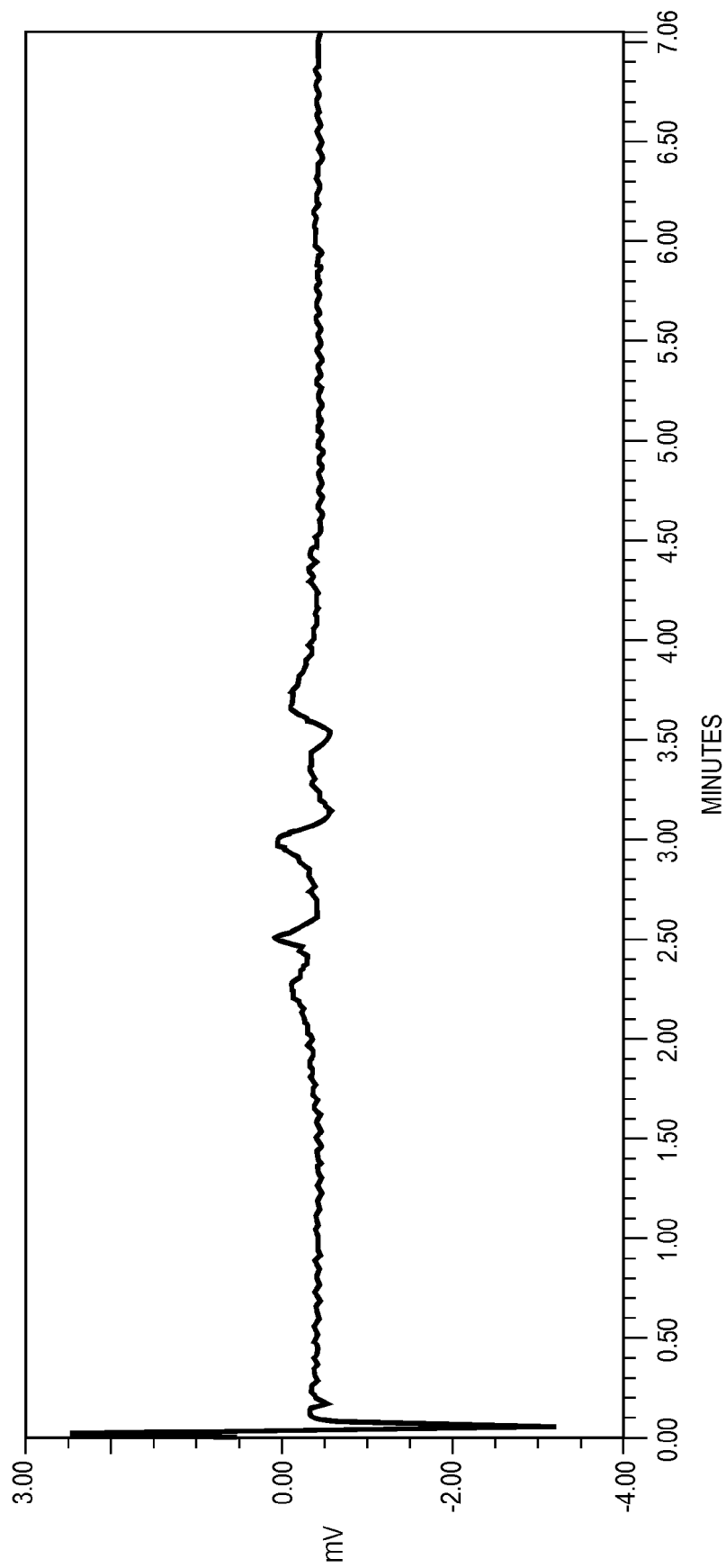
FIG. 9. RP-HPLC trace for unmodified uridine 1 ($R_t$=2.4 min), electrochemical detection at +600 mV.
Figure 10:
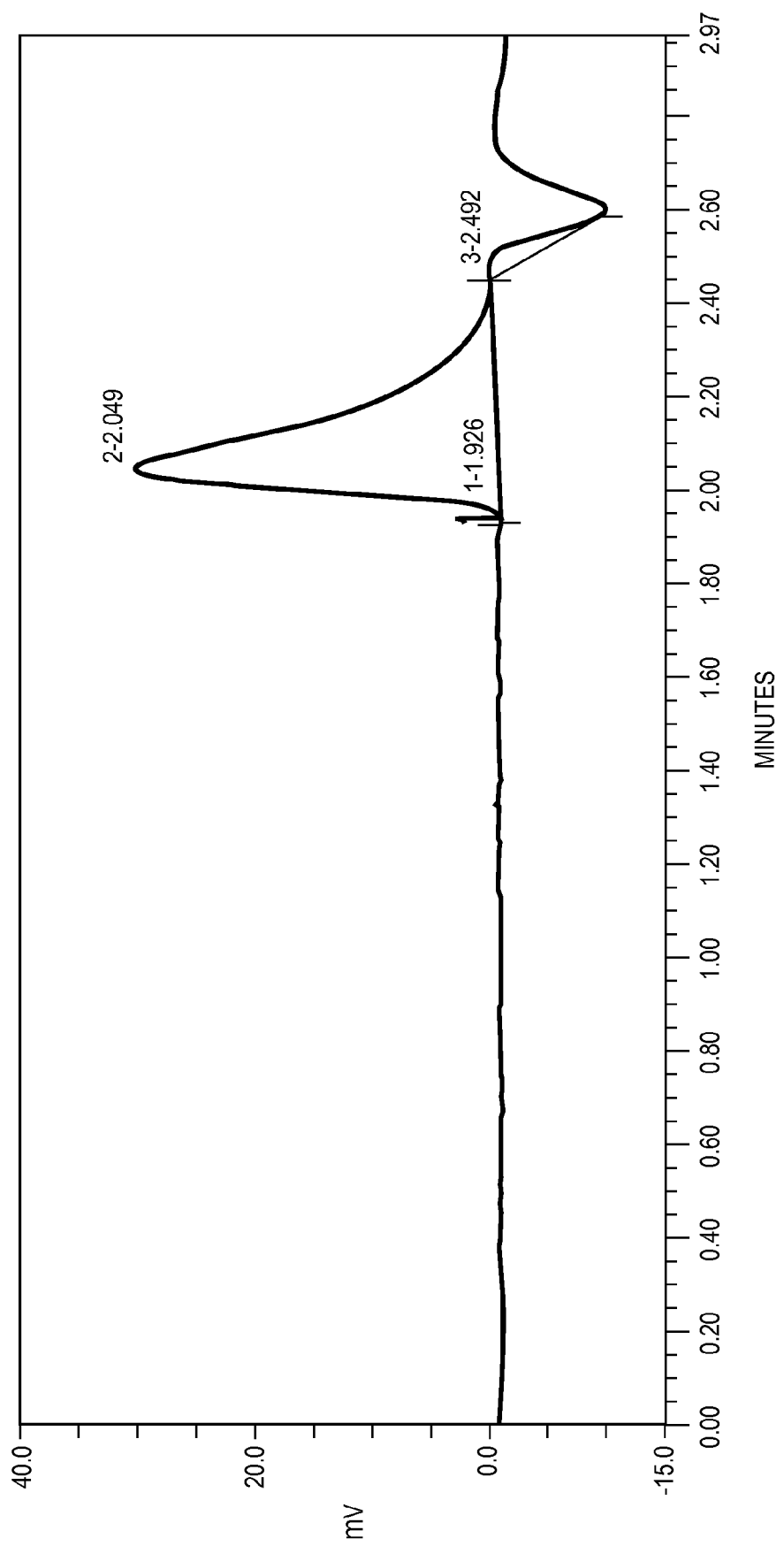
FIG. 10. RP-HPLC trace for carborane containing oligonucleotide 5'-d(CGCTGGTTTGGC($U_2$'-$^{CBM}$)G)-3' (SEQ ID NO:4) (19) ($R_t$=2.05 min), electrochemical detection at +900 mV.
Figure 11:
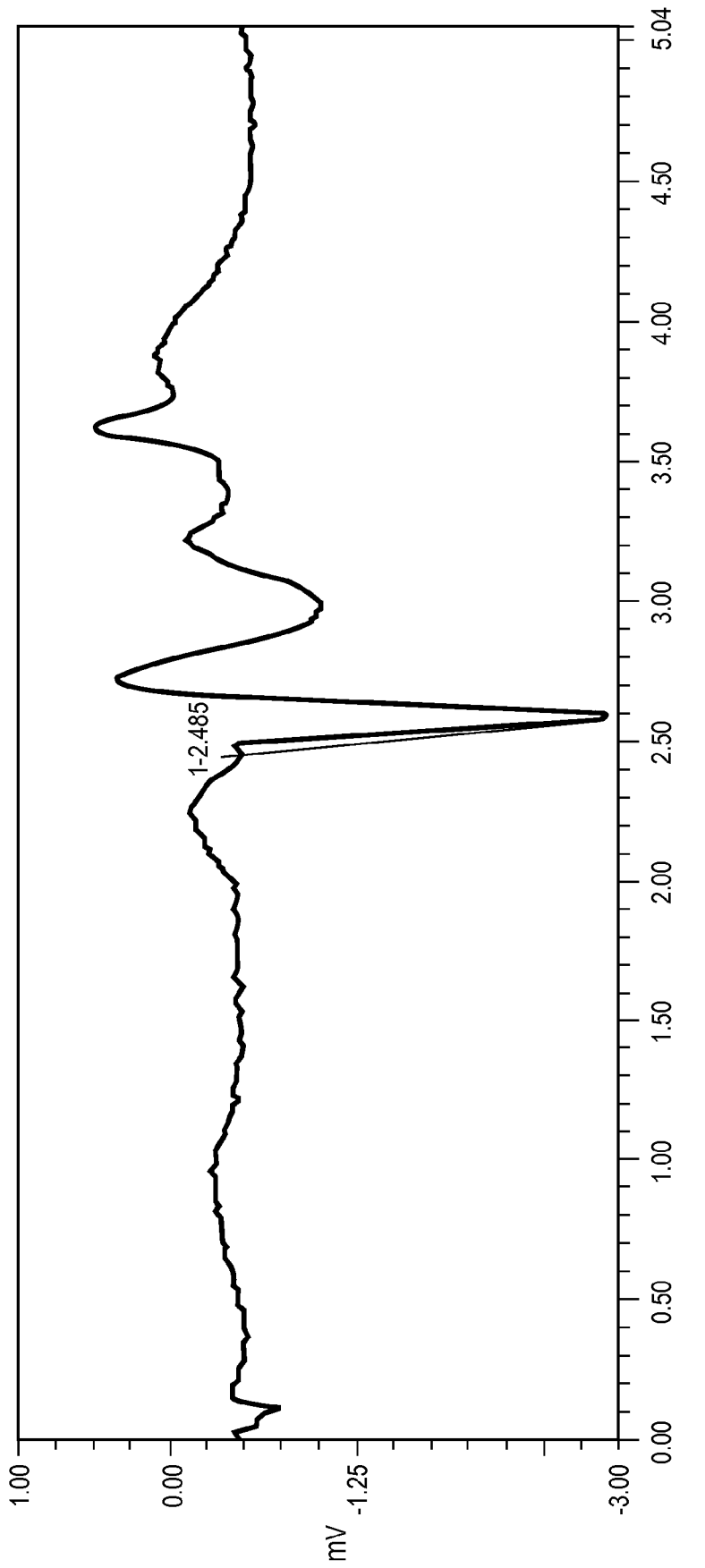
FIG. 11. RP-HPLC trace for unmodified oligonucleotide 15 ($R_t$=2.08 min), electrochemical detection at +900 mV.
Figure 12:
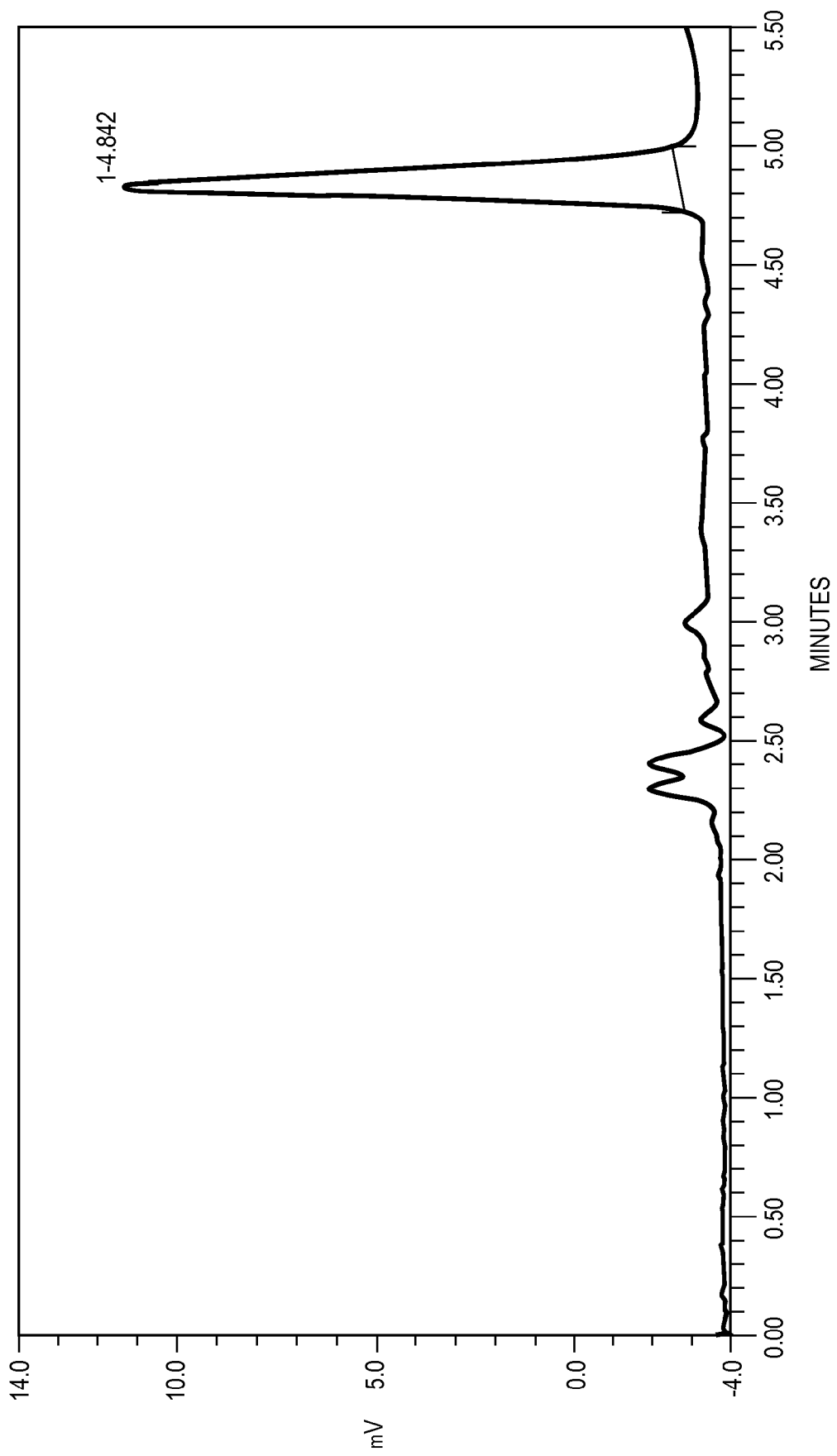
FIG. 12. RP-HPLC trace for 4-O-(diethylenoxy-8-COSAN)thymidine (28b) ($R_t$=4.86 min), electrochemical detection at +1700 mV.
Figure 13:
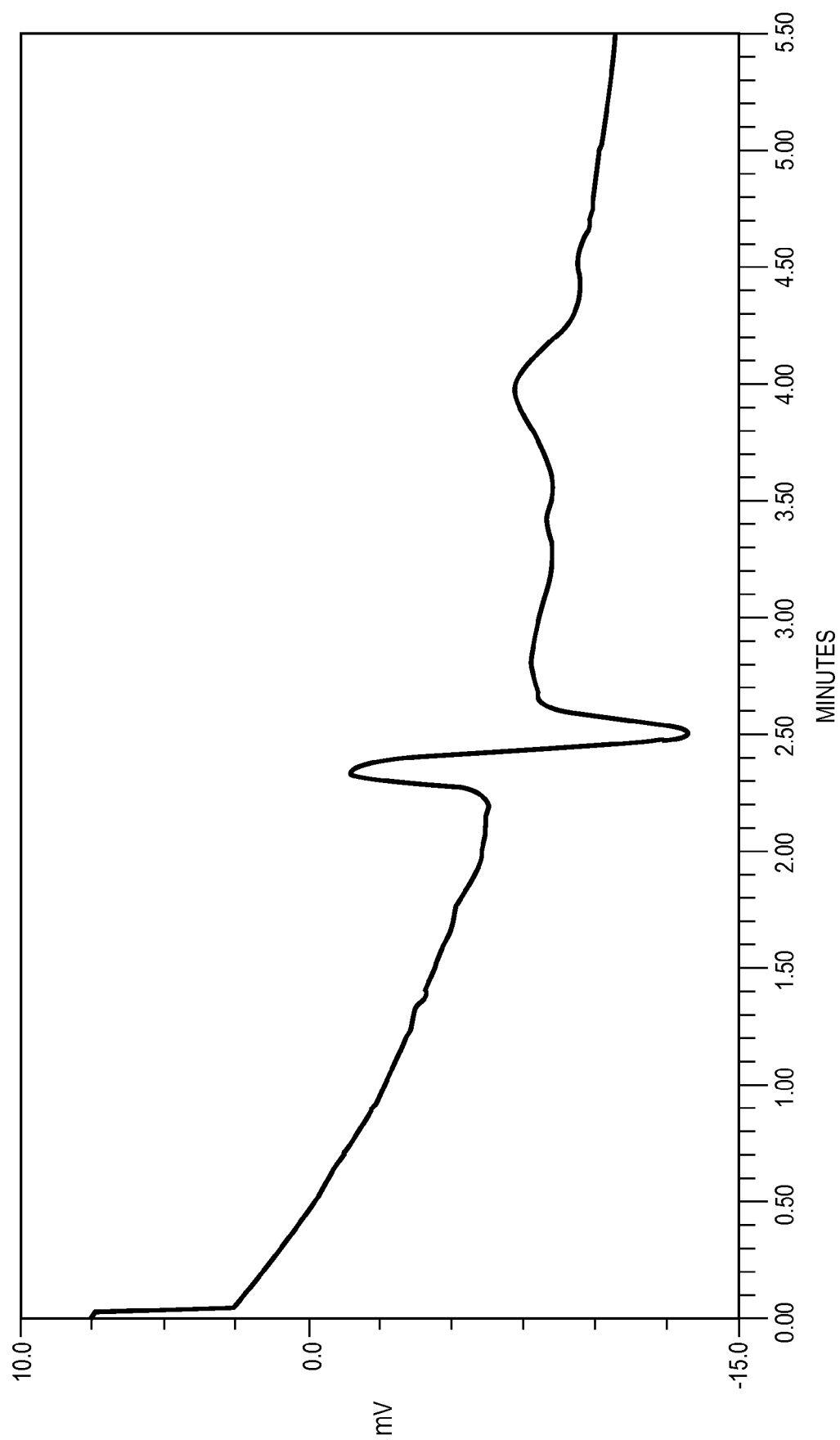
FIG. 13. RP-HPLC trace for unmodified thymidine ($R_t$=2.66 min), electrochemical detection at +1700 mV.

4-O-(diethyleneoxy-8-COSAN)thymidine($^{BEC}$T)-containing tetradecanucleotides 5'-d($^{BEC}$T GCTGGTTTG-GCTG)-3' (SEQ ID NO:2) (8) and unmodified oligonucleotide 5'-d(CGCTGGT7TGGCTG)-3' (9) (SEQ ID NO:3) (FIG. 7).

The natural oligonucleotide 9 and the modified oligonucleotide 8 were synthesized using a Beckman Oligo 1000 DNA synthesizer. Columns loaded with controlled pore glass functionalized with 5'-O-dimethoxytrityl 2'-O-deoxyguanosine mol) were used as a solid support. Suitable 5'-O-dimethoxytrityl-2'-O-deoxynucleoside 3'-(N,N-diisopropyl-beta-cyanoethyl)phosphoramidites (9, B=Gua, Cyt, Thy) were prepared as a 0.5 g/10 mL solution in anhydrous acetonitrile. Elongation of the oligomers with natural nucleotide was performed using a standard 0.2 µmol DNA synthesis beta-cyanoethyl cycle without changes in condensation time. Coupling of the 5'-terminal modified monomer 5'-O-monomethoxytrityl-4-O-(bisethoxy-8-COSAN)thymidine 3'-O-(N,N-diisopropyl-2-cyanoethyl)phosphoramidite (26) as well as oxidation step were performed manually (capping step was omitted). After thirteen coupling cycles, detritylation and washing with acetonitrile the column was detached from the DNA synthesizer and dried under high vacuum (5 min). Monomer 26 (20 mg, 0.02 mmol.) was dissolved in anhydrous acetonitrile (120 µL) followed by addition of tetrazole (0.09 mL, 0.5 M, 0.045 mmol). A solution of activated 26 was applied to the column and the coupling reaction was performed for 30 min. The column was washed with anhydrous acetonitrile (2×5 mL) followed by drying under high vacuum. The oxidation step was performed using a tert-butyl hydroperoxide solution (0.5 M, 1 mL) for 2 min. followed by washing with acetonitrile (1×5 mL) and drying under high vacuum. Oligonucleotides were then cleaved from the support by 1 h incubation with concentrated aqueous ammonia solution (30%, 1 mL) at room temperature then base deprotection was achieved by incubation of resultant solution at 50° C. for 2 h. The solution of crude 5'-O-monomethoxytrityl protected oligonucleotide 8 and 5'-O-dimethoxytrityl protected oligomer 9 was degassed with a stream of argon and evaporated to dryness under vacuum, then redissolved in water. Resultant solution of crude 5'-O-protected oligonucleotides 8 and 9 having 33 and 64 $A_{260}$ optical density units, respectively, were purified using HPLC $C_{18}$ reverse phase column (RP-HPLC) using conditions as follows: 20 min from 0% B to 100% B, 5 min 100% B, 5 min from 100% B to 0% B. Fractions containing the desired product were collected, and the buffer was evaporated under vacuum. The residue was co-evaporated with 96% ethyl alcohol to remove triethylammonium bicarbonate (TEAB), then detritylation was performed using a 80% acetic acid (1.0 mL) at room temperature for 20 min. Next the acetic acid solution was evaporated to dryness under vacuum and the totally deprotected oligonucleotides were purified by RP-HPLC using conditions as above. Buffer A contained 0.1 M TEAB (pH 7.0) in a mixture of acetonitrile and water (2:98, v/v), buffer B contained 0.1 M TEAB (pH 7.0) in a mixture of acetonitrile and water 60:40 (v/v) for modified oligonucleotide 8 (condition I) and 40:60 (v/v) for unmodified oligonucleotide 9 (condition 11). Flow rate 1 mL/min=266 nm. Fractions containing the desired product were collected, and the buffer was evaporated under vacuum. The residue was co-evaporated with 96% ethyl alcohol to remove TEAB. Both oligonucleotides were stored as dry solid at −20° C. When needed, they were redissolved in water, stored as frozen solution, and relyophilized as soon as possible. Yield of purified modified oligonucleotides 8 was 9.1 $A_{260}$ optical density units, and oligonucleotide 9 36.9 $A_{260}$ optical density units, respectively. 8: UV ($H_2O$): $\lambda_{min}$=233.6 nm, $\lambda_{max}$=263.1 nu; RP-HPLC (condition I) $R_f$=18.65 min; 9: UV (H2O): $\lambda_{min}$=230.0 nm, $\lambda_{max}$=257.5; RP-HPLC (condition II) $R_f$=12.32 min; MALDI-MS 4301 [M].

Example procedure for the detection of the nucleoside or oligonucleotide labelled with carborane or metallacarborane group.

Example 5

Electrochemical detection of 2'-O-nido-(o-carboran-1-yl) methyluridine (31).

The stock solution of 31 was prepared by dissolving of compound 31 (7.9 mg, 0.02 mmole) in the mixture of acetonitrile/water (40:60 v/v, 1.5 mL) containing ammonium acetate (0.05 M, pH 5.5), then an aliquot (1 pt) was taken from this solution and was diluted $10^3$-fold with the same as above mixture of solvents up to 1 mL, yielding solution containing 10 ng of compound 31 in 1.9 μl, of solution. From the diluted as above solution an aliquot (1.9 μL) was taken and further diluted 10-folds up to 20 μL with a mixture acetonitrile/water (40:60 v/v) containing ammonium acetate (0.05 M, pH 5.5). A final concentration of 31 was 1.3 μM corresponding to 0.5 ng in 1 μL of solution. This was analyzed by RP-HPLC (Econosil RP $C_{18}$, column, 5 μm, 4.7×250 mm) using an electrochemical detection in the range of potentials from +100 mV to +1400 mV and from −100 mV to −600 mV. As eluent a mixture of acetonitrile/water (40:60 v/v) containing ammonium acetate (0.05 M, pH 5.5) was used. The elution time was 5 min at flow rate 1 mL/min. The analysis was performed at ambient temperature.

Example 6

Control. An approach to electrochemical detection unmodified uridine 1.

The stock solution of uridine (1) was prepared by dissolving I (1 mg, 4 μmole) in a mixture of acetinitrile/water (40:60 v/v, 1 mL) containing ammonium acetate (0.05 M, pH 5.5). From this solution an aliquot was withdrawn (1 μL) then was diluted $10^3$-fold with the same mixture of solvents up to 1 mL yielding solution containing 10 ng of compounds I in 10 μL. From that solution an aliquot was taken (10 μL) then was diluted 2-fold up to 20 μL it by addition of a mixture of acetonitrile/water (40:60 v/v) containing ammonium acetate (0.05 M, pH 5.5). The final solution containing 2.05 μM of nucleoside 1 was analyzed by RP-HPLC (Econosil RP $C_{18}$ column, 5 μm, 4.7×250 mm) using electrochemical detection, the potential range was from +100 mV to +1400 mV and from −100 mV to −600 mV. As an eluent a mixture of acetonitrile/water (40:60 v/v) containing ammonium acetate (0.05 M, pH 5.5) was used. Elution time was S min, and flow rate was 1 mL/min. The elution was performed at ambient temperature.

Example 7

Electrochemical detection of oligonucleotide 5'-d (CGCTGGITTGGCU$_2$'-CBMG)-3' (19) labelled with 2'-O-nido-(o-carboran-1-yl)methyl group.

The stock solution of oligonucleotide 19 was prepared by dissolving 0.05 ODU$_{A260}$ (ca. 1.65 μg, 0.37 nmole) of the oligomer in a mixture of acetonitrile/water (40:60 v/v) (0.5 mL) containing ammonium acetate (0.05 M, pH 5.5) yielding solution containing 3×10 ODU$_{A260}$ (ca. 10 ng) of 19 in 3 μL of solution. From this solution an aliquot (3 μL) was taken and was diluted 7-fold up to 20 μL by addition of a mixture acetonitrile/water (40:60 v/v) containing ammonium acetate (0.05 M, pH 5.5). The final solution containing 0.12 μM of 19 was analyzed by RP-HPLC (Econosil RP $C_{18}$ column, 5 μm, 4.7×250 mm) using electrochemical detection in the potential ranging from +100 mV to +1400 mV and from −100 mV to −600 mV. As eluent a mixture of acetonitrile/water (40:60 v/v) containing ammonium acetate (0.05 M, pH 5.5) was used. The eluting time was 5 min, flow rate was 1 mL/min. The analysis was performed at room temperature.

Example 8

Control. An approach to electrochemical detection of unlabeled oligonucleotide 5'-d(CGCTGGTTTGGCTG)-3' (15).

The stock solution of 15 was prepared by dissolving 0.05 ODU$_{A260}$ (ca. 1.65 μg, 0.38 nmole) of the oligomers 15 in a mixture of acetonitrile/water (40:60 v/v, 0.5 mL) containing ammonium acetate (0.05 M, pH 5.5) yielding solution containing 3×10$^{-4}$ ODU$_{A260}$ (ca. 10 ng, 2.3 μmole) of compound 15 in 3 μL of the solution. From this solution an aliquot (3 μL) was taken and was diluted 7-fold up to 20 μL with a mixture of acetonitrile/water (40:60 v/v) containing ammonium acetate (0.05 M, pH 5.5). The final solution 0.12 μM of 15 was analyzed by RP-HPLC (Econosil RP $C_{18}$ column, 5 μm, 4.7×250 mm) using electrochemical detection in the potential range from +100 mV to +1400 mV and from −100 mV to −600 mV. As eluent a mixture of acetonitrile/water (40:60 v/v) containing ammonium acetate (0.05 M, pH 5.5) was used. The elution time was 5 min, the flow rate was 1 mL/min. The analysis was performed at room temperature.

Example 9

Electrochemical detection of the thymidine labelled with metallacarborane, 4-O-(bisethoxy-8-COSAN)thymidine (28).

The stock solution of compound 28 was obtained by dissolving 28 (0.88 mg, 0.001 mmole) in a mixture of acetonitrile/water (60:40 v/v, 1 mL) containing ammonium acetate (0.05 M, pH 5.5) yielding solution containing 880 ng of 28 in 1 mL of solution. From this solution an aliquot (1 µL) was taken and was diluted 20-fold up 20 µL with a mixture of acetonitrile/water (60:40 v/v) containing ammonium acetate (0.05 M, pH 5.5). The final solution containing 67.5 µM of 28 was analyzed by RP-HPLC system (Fconosil RP $C_{18}$ column, 5 µm, 4.7×250 mm) equipped with electrochemical detector. The potential range was from +100 mV to +2000 mV and from −100 mV to −2000 mV. As eluent a mixture of acetonitrile/water (60:40 v/v) containing ammonium acetate (0.05 M, pH 5.5) was used. The eluting time was 10 min, flow rate 1 mL/min. The analysis was performed at room temperature.

Example 10

Control. An approach to electrochemical detection of unlabeled thymidine

The stock solution of thymidine was prepared by dissolving thymidine (1 mg, 4.4 µmole) in a mixture of acetonitrile/water (60:40 v/v, 1 mL) containing ammonium acetate (0.05 M, pH 5.5) yielding a solution containing 1 µg of thymidine in 1 µL of solution. From this solution an aliquot was taken (1 µL) and was diluted up to 1 mL with the same mixture of solvents yielding solution containing 10 ng of thymidine in 10 µL of solution, next this solution was further diluted 2-fold up to 20 µL with same mixture of solvents. The final solution containing 2.2 µM of thymidine was analyzed RP-HPLC (Econosil RP $C_{18}$ column, 5 µm, 4.7×250 mm) using electrochemical detection in the range of the potentials from +100 mV to +2000 mV and from −100 mV to −2000 mV. As eluent a mixture of acetonitrile/water (60:40 v/v) containing ammonium acetate (0.05 M, pH 5.5) was used. Elution time was 10 min, flow rate was 1 mL/min. The analysis was performed at room temperature.

Cited References

Agrawal, S., ed., Antisense Therapeutics. (1996). Humana Press, Totowa, N.J.

Agrawal, S., ed., Protocols for Oligonucleotides and Analogs. Synthesis and Properties. (1993). Humana Press Inc., Totowa, N.J.

Anthony, R. M., Brown, T. J., French, G. L., DNA array technology and diagnostic microbiology. (2001). Expert. Rev. Mol. Diagn., 1, 30-38.

Bigey P., Hoist Sonnichsen, S., Meunier, B., Nielsen, P. E. DNA binding and cleavage by a cationic manganese porphirin-peptide nucleic acid conjugate. Bioconjugate Chem., 8, 267-270, (1997).

Cotter, F. E., ed., Molecular Diagnosis of Cancer. (1996). Humana Press, Totowa, N.J.

Crooke, S. T. Therapeutic Applications of Oligonucleotides. (1995). Springer-Verlag, N.Y.

Denhardt, D. T. A membrane filter technique for the detection of complementary DNA. (1966).

Biochem. Biophys. Res. Commun., 23, 641-646.

Dougan, H., Hobbs, J. B., Weitz, J. I., Lyster, D. M. Synthesis and radioiodination of stannyl oligodeoxyribonucleotide. Nucl. Acids. Res., 25, 2897-2901, (1997).

Dubey, I., Pratviel, G., Meunier, B. Synthesis and DNA cleavage of 2'-O-amino4iked metalloporphirin-oligonucleotide conjugates. J. Chem. Soc. Perkin Transactions, Iss 18, 3088-3095, (2000).

Ehrlich, G. D., Greenberg, S. J. PCR-Based Diagnostics in Infectious Disease. (1994). Blackwell Scientific Publications, Oxford, UK.

Elles, R., ed., Molecular Diagnosis of Genetic Diseases. (1996). Humana Press, Totowa, N.J.

Fulcrand-El Kattan, G., Lesnikowski, Z. J., Yao, S., Tanious, F., Wilson, W. D., Shinazi, R. F. Carboranyl Oligonucleotides. 2. Synthesis and Physicochemical Properties of Dodecathymidylate Containing 5-(o-Carboranyl-1-yl)-2'-O-Deoxyuridine. J. Am. Chem. Soc., 116, 7494-7501, (1994).

Grimes, R. N. "Transition Metal Metallacarboranes" in "Comprehensive organometallic Chemistry II", Vol. 1. (1995). Housecroft, C. E., ed. Pergamon, pp. 373-430.

Hall I. H., Tolmie C. E., Barnes B. J., Curtis M. A., Russell J. M., Finn M. G., Grimes R. N. Cytotoxicity of tantalum (V) and niobium (V) small carborane complexes and mode of action in P388 lyphocytic leukemia cells. Applied Organometallic Chem., 14, 108-118, (2000).

Hall, B. D., Spiegelman, S. Sequence complementarity of T2-DNA and T2-specific RNA. (1961). Proc. Natl. Acad. Sci. USA, 47, 137-146.

Hoheisel, J. D., Oligomer-chip technology. (1997). TIBTECH, 15, 465-469.

Hosmane, N. S., Maguire, J. A. "Recent Advances in the Chemistry of Main Group Heterocarboranes" in "Advances in Boron and the Boranes". (1987). Liebman, J. F., Greenberg, A., Williams, R. E., ed. VCH., str. 297-329.

Housecroft, C. E. Boranes and metalloboranes—Structure, bonding and reactivity. (1990). John Wiley and Sons, New York, N.Y.

Hurley, D. J., Tor, Y. Metal-containing oligonucleotides: Solid-Phase synthesis and luminescence properties. J. Am. Chem. Soc., 120, 2194-2195, (1998).

Ihara, T., Maruo, Y., Takenaka, S., Takagi, M. (1996). Ferocene-oligonucleotide conjugates for electrochemical probing of DNA. (1996). Nucl. Acids Res., 24, 42734280.

Ihara, T., Nakayama, M., Murata, M., Maeda, M., Gene sensor using ferrocenyl oligonucleotide. (1997). Chem. Commun., 1609-1610.

Jefferies D. J., De Clerq, E., ed., Antiviral Chemotherapy. (1995). John Wiley and Sons, Chichester UK.

Keller, G. H., Manak, M. M. DNA Probes. Background, applications and procedures. (1993). M Stockton Press, New York, N.Y.

Lesnikowski, Z. J. and Schinazi, R. F. Boron Neutron Capture Therapy of Cancers: Nucleic Bases, Nucleosides, and Oligonucleotides as Potential Boron Carriers. Polish. J. Chem. 69, 827-840 (1995).

Lesnikowski, Z. J., Fulcrand-El Kattan, G., Lloyd, R. M. Jr., Juodawikis A., Schinazi R. F. Carboranyl Oligonucleotides. 3. Biochemical Properties of Oligonucleotides Containing 5-(o-carboranyl-1-yl)-2'-deoxyuridine. Biochemistry, 35, 5741-5746, (1996b).

Lesnikowski, Z. J., Fulcrand-El Kattan, G., Lloyd, R. M. Jr., Schinazi, R. F. Biological Properties of Dodeca(thymidine phosphates) Containing 5-(o-Carboran-1-yl)-2'-deoxyuridine. Phosphorus, Sulfur, and Silicon, 109-110, 385-388, (1996a).

Lesnikowski, Z. J., Lloyd, R. M. Jr., Schinazi, R. F. Comparison of Physicochemical Properties of (o-Carboran-1-yl) methylphosphonate and Methylphosphonate Oligo-nucleotides. Nucleosides and Nucleotides, 16, 1503-1505 (1997).

Lesnikowski, Z. J., Schinazi, R. F. Boron Containing Oligonucleotides. Nucleosides and Nucleotides, 17, 635-648 (1998).

Lesnikowski, Z. J., Schinazi, R. F. Carboranyl Oligonucleotides. 1. Synthesis of Thymidine(3',5')thymidine (o-carboranyl-1-yl)methylphosphonate. J. Org. Chem., 58: 6531-6534, (1993).

Lesnikowski, Z. J., Shi J., Schinazi R. F. Nucleic acids and nucleosides containing carboranes. J. Organomet. Chem., 581, 156-169 (1999).

Lipshuth, J., Morris, D., Chee, M., Hubbell, E., Kozal, M. J>, Shah, N., Shen, N., Yang, R., Fodor, S. P. A., Using oligonucleotide probe arrays to access genetic diversity. (1995). BioTechniques, 19, 442-447.

Mack, D. P., Iverson, B. L., Dervan, P. B. Design and chemical synthesis of a sequence-specific DNA-cleaving protein. J. Am. Chem. Soc., 110, 7572-7474, (1988).

Micklefield, J., Backbone modification of nucleic acids: Synthesis, structure and therapeutic applications. Current Med. Chem., 8, 1157-1179 (2001).

Niemeyer, C. M. DNA as a Material for Nanotechnology. Angew. Chem. Int. Ed. Engl., 36, 585-587 (1997).

Olejniczak A. B., Koziolkiewicz M., Lesnikowski Z. J., Carboranyl oligonucleotides. 4.

Synthesis, and physicochemical studies of oligonucleotides containing 2'-O-(o-carboran-1-yl)methyl group, Antisense Nucl. Acid Drug Develop., 2002, 12, 79-94.

Ossipov, D., Pradeepkumar, P. I., Holmer, M., Chattopadhyaya, J. Synthesis of [Ru(phen)$_2$dppz]$^2$+tethered oligo-DNA and studies on the metallointercalation mode into the DNA duplex. J. Am. Chem. Soc., 123, 3551-3562 (2001).

Sanghvi Y. S., Cook, P. D., ed., Carbohydrate Modifications in antisense research. (1994). American Chemical Society, Washington, D.C.

Saxena A. K., Hosmane N. S. Recent Advances in the Chemistry of Carborane Metal Complexes Incorporating d- and f-Block Elements. Chem. Rev., 93, 1081-1124, (1993).

Schinazi, R. F, Fulcrand-El Kattan, G., Legnikowski, Z. J. Nucleosides and oligonucleotides containing boron clusters. U.S. Pat. No. 6,180,766 (2001).

Schinazi, R. F., Lesnikowski, Z. J., Fulcrand-El Kattan, G., Wilson, W. D. Carboranyl Oligonucleotides for Antisense Technology and Boron Neutron Capture Therapy of Cancers. American Chemical Society Symposium Series, Vol. 580, Carbohydrate Modifications in Antisense Research, Sanghvi Y S, Cook P D, Eds., Chapter 11, pp. 169-182 (1994).

Seeman, N., Wang Hui, et al., New motifs in DNA nanotechnology. (1998). Nantechenology 9, 257-273 (1998).

Shabarova, Z., and Bogdanov, A. Advanced Organic Chemistry of Nucleic Acids. (1994). VCH, Weinheim.

Singhal, P., Kuhr, W. G. Ultrasensitive voltametric detection of underivatized oligonucleotides and DNA. (1997). Ana. Chem., 69, 4828-4832.

Steel, A. B., Heme, M. T., Tarlov, M. J. Electrochemical quantitation of DNA immobilized on gold. (1998). Anal. Chem., 70, 4670-4677.

Strobel, S. A., Heinz, E. M., Dervan, P. B. Double-strabd cleavage of genomic DNA at a single site by triple-helix formation. J. Am. Chem. Soc., 110, 7927-7929, (1988).

Takenaka, S., Uto, Y., Kondo, H., Ihara, T., Takagi, M. Electrochemically active DNA probes: Detection of target DNA sequences at femtomole level by High-Performance Liquid Chromatography with electrochemical detection. (1994). Anal. Biochem., 218, 436-443.

Tjarks, W., The use of boron clusters in the rational design of boronated nucleosides for neutron capture therapy of cancer. J. Organomet. Chem., 614615, 3747 (2000).

Uhlnann, E., Peyman, A. Antisense oligonucleotides—A new therapeutic principle. Chem. Rev., 90, 543-584, (1990).

Wang, J., Cai, X., Fernandez, J. R., Grant, D. H., Ozsoz, M. Electrochemical measurements of oligonucleotides in the presence of chromosomal DNA using membrane-covered carbon electrode. (1997). 69, 40564059.

Wiedbrauuk, D. L., Farkas, D. H., ed., Molecular Methods for Virus detection. (1995). Academic Press, Inc., San Diego, Calif.

Yu, C. J., Yowanto, H., Wan, Y., Meade, T. J., Chong, Y., Strong, M., Donilon, L. H., Kayyem, J. F., Gozin, M., Blackburn, G. F. Uridine-conjugated ferrocene DNA oligonucleotides: unexpected cyclization reaction of the uridine base. J. Am. Chem. Soc., 122, 6767-6768, (2000).

The invention claimed is:

1. A modified nucleoside comprising:
   a nucleoside consisting of a nucleic acid base and one of a sugar residue or an analogue of a sugar residue; and
   at least one metallocarborane group including at least one metal ion, wherein each metallocarborane group is attached through a linker to the nucleic acid base or the sugar residue or the analogue of a sugar residue.

2. The modified nucleoside of claim 1, wherein the linker is attached to the nucleoside through at least one of a hydroxy group of the nucleic acid base, a hydroxy group of the sugar residue or the sugar residue analogue, and an amino group of the nucleic acid base.

3. The modified nucleoside of claim 1, wherein the nucleic acid base is selected from the group consisting of a thymine, a uracil, a 5-halouracil, a cytosine, a 5-halocytosine, an adenine, a guanine, a 2,6-diaminopurine, a 2-amino-6-chloropurine, a 2-aminopurine, a 5-alkyluracil, a 5-alkylcytosine, a 2-thiouracil, a 2,4-dithiouracil, and a 4-thiouracil.

4. The modified nucleoside of claim 1, wherein the metal ion is selected from the group consisting of Sn, Mn, Tc, Re, Fe, Ru, Os, Co, Rh, Ir, Ni, Pd, Pt, Cu, Ag, Au, Sc, Cr, Mg, Zr, Mo, Sm, Yb, Hf, W, Hg, Gd, U and Y.

5. The modified nucleoside of claim 1, wherein the linker is selected from the group consisting of:
   (i) $—[(CH_2)_n—(W)_m]_k—$
   wherein n is an integer in a range of 0 to 5, m is either 0 or 1, k is an integer in a range of 1 to 6, and W is O, S, S(O), $S(O)_2$, Se, or NR, wherein R is H, alkyl, haloalkyl, alkoxyalkyl, or aryl;
   (ii) X—P(Z)(Y)O
   wherein X is O, S, or Se, Z is O, S, or Se, Y is OH, SH, SeH, alkyl, haloalkyl, alkoxyalkyl, aryl, or halogen;
   (iii) CH=CH;
   (iv) CC;
   (v) NN;
   (vi) CHOH; and
   (vii) $CHN_3$.

6. The modified nucleoside of claim 1, wherein the at least one metallocarborane group is {8-[(1,2-dicarba-closo-undecaboranyl)-3,3'-A-(1',2'-dicarba-closo-undecaboranyl)atyl]} or {8-[(1,2-dicarba-closo-undecaboranyl)-3-A-cyclopentadienyl]atyl}, wherein A is a metal ion.

7. The modified nucleoside of claim 1, wherein the at least one metallocarborane group is {8-[(1,2-dicarba-closo-undecaboranyl)-3,3'-cobalt-(1',2'-dicarba-closo-undecaboranyeatyl]} or {8-[(1,2-dicarba-closo-undecaboranyl)-3-cobalt-cyclopentadienyl]atyl}.

8. The modified nucleoside of claim 1, wherein the at least one metallocarborane group is selected from the group consisting of a 3N-{diethyleneoxy-{8-[(1,2-dicarba-closo-undecaboranyl)-3,3'-cobalt-(1',2'-dicarba-closo-undecaboranyl)atyl]} and a 4O-{diethyleneoxy-{8-[(1,2-dicarba-closo-undecaboranyl)-3,3'-cobalt-(1',2'-dicarba-closo-undecaboranyl)atyl]}.

9. The modified nucleoside of claim 1, wherein the sugar residue analogue comprises a sugar residue with at least one hydroxyl group replaced by a member selected from the group consisting of:
(i) —OP(Z)(Y)X, where Z is O, S, or Se, Y is OH, SH, SeH, alkyl, haloalkyl, alkoxyalkyl, aryl or halogen, X is OH, SH, SeH, alkyl, haloalkyl, alkoxyalkyl, aryl or halogen; and
(ii) —OP(Y)X, where Y is alkyl, haloalkyl, alkoxyalkyl, (—O-alkyl), aryl, aryloxyaryl, (—O-aryl), $NR_2$, or halogen, X is alkyl, haloalkyl, alkoxyalkyl, (—O-alkyl), aryl, aryloxyaryl, (—O-aryl), $NR_2$ or halogen, wherein each R is independently H, alkyl, haloalkyl, alkoxyalkyl, or aryl.

10. The modified nucleoside of claim 1, wherein the linker is attached to the nucleoside through at least one of a 3' hydroxy group, a 5' hydroxy group and a 2' hydroxy group of the sugar residue or the analogue of the sugar residue.

11. The modified nucleoside of claim 1, further comprising wherein the nucleoside sugar residue is attached to a phosphate group selected from the group consisting of a monophosphate, a diphosphate, and a triphosphate and the metallocarborane group is attached through the linker to a phosphorus atom of the monophosphate group or an oligophosphate group.

12. The modified nucleoside of claim 1, wherein the nucleic acid base further comprises an amino group protected with a protecting group suitable for synthesis of DNA-oligonucleotides or RNA-oligonucleotides.

13. The modified nucleoside of claim 1, wherein the sugar residue further comprises at least one free hydroxyl group protected with a protecting group suitable for synthesis of DNA-oligonucleotides or RNA-oligonucleotides.

14. The nucleoside of claim 1, wherein the metal ion is selected from the group consisting of Fe, Co, Ru, and Rh.

15. A compound selected from the group consisting of:
(i) 5'-O-monomethoxytrityl-3'-O-acetyl-3-N-(diethyleneoxy-8-COSAN)-thymidine;
(ii) 5'-O-monomethoxytrityl-3'-O-acetyl-4-O-(diethyleneoxy-8-COSAN)-thymidine;
(iii) 4-O-(diethyleneoxy-8-COSAN)-thymidine;
(iv) 8-dioxanyl-O-COSAN;
(v) 5'-O-monomethoxytrityl-4-O-(diethyleneoxy-8-COSAN)-thymidine;
(vi) 5'-O-monomethoxytrityl-4-O-(diethyleneoxy-8-COSAN)-thymidine 3'-O—(N,N-diisopropyl-beta-cyanoethyl)-amidophosphonate, and
wherein COSAN is -{[(1,2-dicarba-closo-undecaboranyl)-3,3'-cobalt-(1',2'-dicarba-closo-undecaboranyl)]atyl}-.

16. A modified oligonucleotide comprising:
an oligonucleotide consisting of a chain of nucleotides; and
at least one metallocarborane group including at least one metal ion, wherein each metallocarborane group is attached through a linker to a nucleic acid base, an internucleotide linkage or a sugar residue.

17. The modified oligonucleotide of claim 16, wherein the at least one metallocarborane group is attached to a 3'-terminal nucleotide or a 5'-terminal nucleotide.

18. The modified oligonucleotide of claim 16, wherein the at least one metallocarborane group is attached to a 3'-fragment of the oligonucleotide or a 5'-fragment of the oligonucleotide.

19. The modified oligonucleotide of claim 16, wherein the at least one metallocarborane group is attached to an internal nucleotide of the oligonucleotide.

20. The modified oligonucleotide of claim 16, wherein the metal ion is selected from the group consisting of Sn, Mn, Tc, Re, Fe, Ru, Os, Co, Rh, Ir, Ni, Pd, Pt, Cu, Ag, Au, Sc, Cr, Mg, Zr, Mo, Sm, Yb, Hf, W, Hg, Gd, U and Y.

21. The modified oligonucleotide of claim 16, wherein the linker is selected from the group consisting of:
(i) —[$(CH_2)_n(W)_m$]$_k$—
wherein n is an integer in a range of 0 to 5, m is either 0 or 1, k is an integer in a range of 1 to 6, and W is O, S, S(O), $S(O)_2$, Se, or NR, wherein R is H, alkyl, haloalkyl, alkoxyalkyl, or aryl;
(ii) X—P(Z)(Y)O
wherein X is O, S, or Se, Z is O, S, or Se, Y is OH, SH, SeH, alkyl, haloalkyl, alkoxyalkyl, aryl, or halogen;
(iii) CH=CH;
(iv) CC;
(v) NN;
(vi) CHOH; and
(vii) $CHN_3$.

22. The modified oligonucleotide of claim 16, wherein the at least one metallocarborane group is -{8-[(1,2-dicarba-closo-undecaboranyl)-3,3'-A-(1',2'-dicarba-closo-undecaboranyl)atyl]}- or -{8-[(1,2-dicarba-closo-undecaboranyl)-3-A-cyclopentadienyl]atyl}-, wherein A is the at least one metal ion.

23. The modified oligonucleotide of claim 16, wherein the at least one metallocarborane group is -{8-[(1,2-dicarba-closo-undecaboranyl)-3,3'-cobalt-(1',2'-dicarba-closo-undecaboranyl)atyl]}- or -{8-[(1,2-dicarba-closo-undecaboranyl)-3-cobalt-cyclopentadienyl]atyl}-.

24. The modified oligonucleotide of claim 16, wherein the oligonucleotide comprises -{diethyleneoxy-{8-[(1,2-dicarba-closo-undecaboranyl)-3,3'-cobalt-(1',2'-dicarba-closo-undecaboranyl)atyl]}- group attached to the 2O position, the 4O position, or the 3N position of the pyrimidine ring.

25. The modified oligonucleotide of claim 16, further comprising 3N-(diethyleneoxy-8-COSAN) thymidine ($^{BCCo}$T) or 4O-(diethyleneoxy-8-COSAN) thymidine ($^{BCCo}$T), wherein COSAN is -{[(1,2-dicarba-closo-undecaboranyl)-3,3'-cobalt-(1',2'-dicarba-closo-undecaboranyl)]atyl}-, and a sequence of ($^{BCCo}$T) is 5'-d($^{BCCo}$TGCTGGTTTGGCTG)-3' (SEQ ID NO: 1).

26. The modified oligonucleotide of claim 16, wherein the oligonucleotide is capable of hybridization to a complementary DNA or RNA strand.

27. The modified oligonucleotide of claim 16, wherein the oligonucleotide is capable of hybridization to a double stranded DNA.

28. A method for detecting a labeled compound selected from a modified nucleoside, a modified nucleotide and a modified oligonucleotide, comprising:
electrochemically detecting ametallocarborane group in a modified nucleoside of claim 1 incorporated therein.

29. The method of claim 28, wherein the labeled compound comprises the modified oligonucleotide.

30. The method of claim 28, wherein the step of electrochemically detecting further comprises employing the labeled compound as a molecular probe.

31. The method of claim 28, wherein the step of electrochemically detecting further comprises employing the labeled compound as a material for nanotechnology, construction of a microarray or DNA sensors.

32. The method of claim 28, further comprising immobilizing the labeled compound on an electrode.

33. The method of claim 28, wherein the labeled compound comprises the modified nucleotide.

* * * * *